(12) United States Patent
Taniguchi et al.

(10) Patent No.: US 12,102,287 B2
(45) Date of Patent: Oct. 1, 2024

(54) ENDOSCOPIC HOOD AND ENDOSCOPE

(71) Applicant: NISSHA CO., LTD., Kyoto (JP)

(72) Inventors: Chuzo Taniguchi, Kyoto (JP); Ryomei Omote, Kyoto (JP); Junichi Shibata, Kyoto (JP); Yoshiro Fujii, Kyoto (JP)

(73) Assignee: NISSHA CO., LTD, Kyoto (JP)

( * ) Notice: Subject to any disclaimer, the term of this patent is extended or adjusted under 35 U.S.C. 154(b) by 0 days.

(21) Appl. No.: 18/572,686

(22) PCT Filed: Mar. 30, 2022

(86) PCT No.: PCT/JP2022/016312
§ 371 (c)(1),
(2) Date: Dec. 20, 2023

(87) PCT Pub. No.: WO2022/270116
PCT Pub. Date: Dec. 29, 2022

(65) Prior Publication Data
US 2024/0260815 A1  Aug. 8, 2024

(30) Foreign Application Priority Data

Jun. 23, 2021 (JP) ................................. 2021-103809

(51) Int. Cl.
*A61B 1/00* (2006.01)
*A61B 1/012* (2006.01)

(52) U.S. Cl.
CPC ........ *A61B 1/00089* (2013.01); *A61B 1/0011* (2013.01); *A61B 1/00114* (2013.01); *A61B 1/012* (2013.01)

(58) Field of Classification Search
CPC .............. A61B 1/00089; A61B 1/0011; A61B 1/00114; A61B 1/012
See application file for complete search history.

(56) References Cited

U.S. PATENT DOCUMENTS

| 5,759,150 A * | 6/1998 | Konou ............... A61B 18/1485 |
| | | 600/114 |
| 2005/0080411 A1 * | 4/2005 | Ouchi ................ A61B 18/1492 |
| | | 606/45 |

(Continued)

FOREIGN PATENT DOCUMENTS

| JP | 2004261581 A | 9/2004 |
| JP | 2005168927 A | 6/2005 |

(Continued)

*Primary Examiner* — Aaron B Fairchild
(74) *Attorney, Agent, or Firm* — Alleman Hall & Tuttle LLP

(57) ABSTRACT

An endoscopic hood and an endoscope to which the endoscopic hood is attached improve visibility for the user. The endoscopic hood includes a body formed of a transparent cylinder having two open ends and a conductive film embedded integrally in the body. The conductive film includes a transparent film and a transparent electrode pattern on the transparent film. The transparent electrode pattern includes a transparent electrode, a transparent wire portion extending from the transparent electrode, and a transparent terminal at an end of the transparent wire portion. The transparent terminal is exposed from the body. The endoscope includes an insertion portion insertable into a body of a subject, the endoscopic hood attached to a distal end of the insertion portion, and at least one wire having one end electrically connected to the transparent terminal and another end electrically connected to an external device.

10 Claims, 16 Drawing Sheets

(56) References Cited

U.S. PATENT DOCUMENTS

2006/0030844 A1* 2/2006 Knight ............... A61B 18/1492
606/41
2016/0353978 A1* 12/2016 Miller ................ A61B 1/00096

FOREIGN PATENT DOCUMENTS

| JP | 2007082767 A | 4/2007 |
| JP | 2007089733 A | 4/2007 |
| JP | 2010158565 A | 7/2010 |
| JP | 2018524131 A | 8/2018 |
| KR | 1020160031787 A | 3/2016 |

* cited by examiner

FIG. 16A         CONVENTIONAL ART
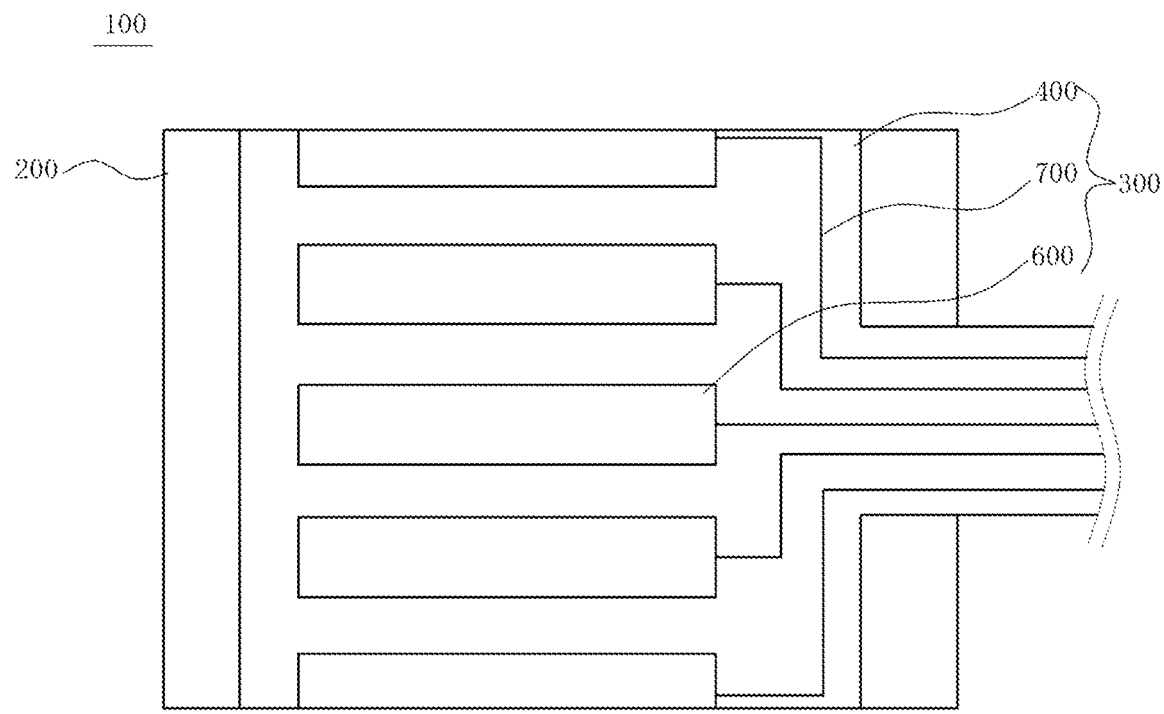
FIG. 16B         CONVENTIONAL ART
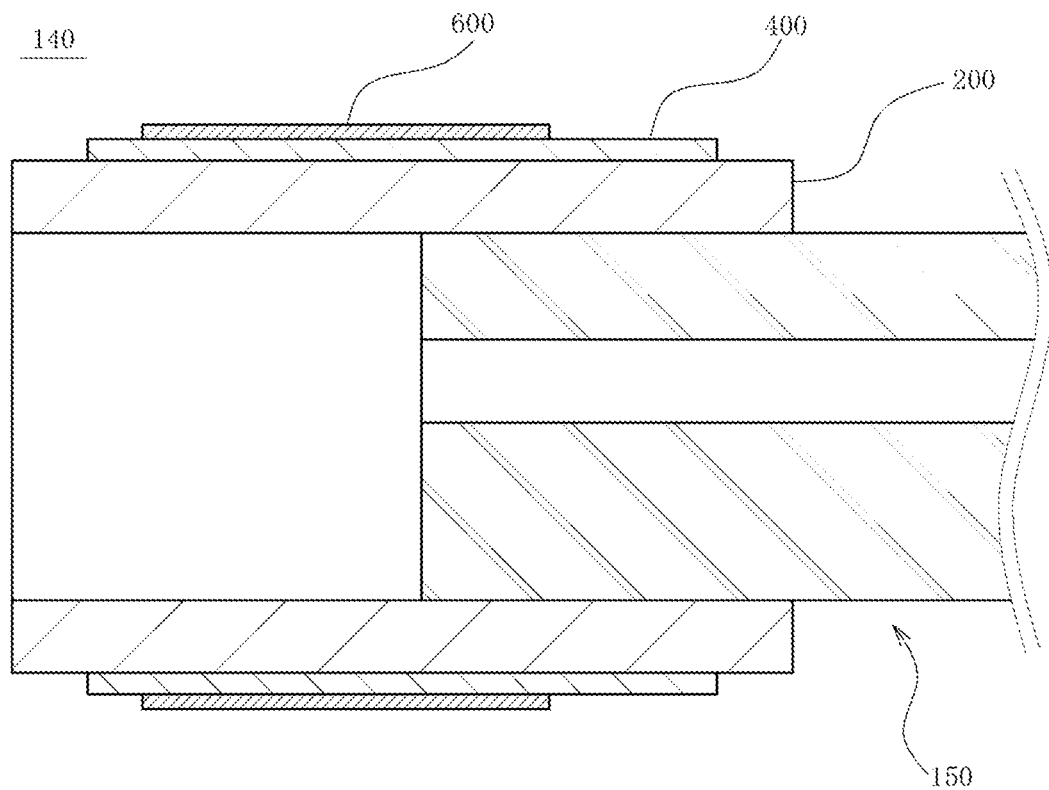

ENDOSCOPIC HOOD AND ENDOSCOPE

TECHNICAL FIELD

The present invention relates to an endoscopic hood and an endoscope.

BACKGROUND

A known cylindrical hood formed from a transparent resin is attachable to the distal end of an insertion portion of an endoscope. The hood attached to the endoscope easily maintains an appropriate distance from the insertion portion to body tissue. The hood can also protect the insertion portion from being contaminated with, for example, body fluids, and can maintain the field of view of the user. Such an endoscopic hood may additionally have electrical functions.

As shown in FIG. 16A, Patent Literature 1 describes an endoscopic hood 100 including a cylindrical body 200 formed from a hard resin with a conductive film 300 bonded to its outer circumferential surface. The conductive film 300 includes multiple electrodes 600 and multiple wire portions 700 on a transparent film 400. The use of the endoscopic hood 100 will be described with reference to FIG. 16B. The endoscopic hood 100 is first attached to the distal end of an insertion portion 150 of an endoscope 140. The wire portions 700 are then electrically connected to a high-frequency generator (not shown) with wires (not shown). After the electrodes 600 are placed into contact with diseased tissue, the high-frequency generator is turned on to allow a current to flow through the electrodes 600. The diseased tissue then undergoes ablation with the current. The user of the endoscopic hood 100 can perform ablation while viewing the tissue through the spaces between the electrodes 600.

CITATION LIST

Patent Literature

Patent Literature 1: Japanese Unexamined Patent Application Publication No. 2004-261581

BRIEF SUMMARY

Technical Problem

Such a known endoscopic hood includes opaque electrodes and thus has two issues below. First, the user may be exposed to the glare of light reflected off the electrodes after being emitted from the endoscope. Second, the field of view of the user may be obstructed by the opaque electrodes. In other words, the visibility for the user may be reduced by the known hood for an endoscope.

In response to the above issues, one or more aspects of the present invention are directed to an endoscopic hood that improves visibility for the user and to an endoscope to which the endoscopic hood is attached.

Solution to Problem

An endoscopic hood according to a first aspect is attachable to a distal end of an insertion portion of an endoscope. The endoscopic hood includes a body formed of a transparent cylinder having two open ends and a conductive film embedded integrally in the body. The conductive film includes a transparent film and a transparent electrode pattern on the transparent film. The transparent electrode pattern includes a transparent electrode, a transparent wire portion extending from the transparent electrode, and a transparent terminal at an end of the transparent wire portion. The transparent terminal is exposed from the body.

The endoscopic hood with the above structure is fully transparent. Thus, the endoscopic hood is less likely to reflect light traveling from the endoscope and is less likely to obstruct the field of view of the user with the electrode pattern. This improves visibility for the user in, for example, an endoscopic examination.

Additionally, the conductive film is embedded integrally in the body to reduce the likelihood of entry of, for example, body fluids through an end face of the conductive film. Thus, the conductive film is less likely to peel off from the body than a conductive film bonded to the body.

An endoscopic hood according to a second aspect is the endoscopic hood according to the first aspect in which the transparent electrode pattern is a mesh electrode pattern including a plurality of thin wires or a vapor deposition electrode pattern including a vapor deposition layer.

An endoscopic hood according to a third aspect is the endoscopic hood according to the first aspect or the second aspect in which the transparent electrode pattern is provided on a surface of the transparent film, and the conductive film is embedded integrally in the body with the transparent film exposed on an inner circumferential surface of the body and the transparent electrode pattern facing outside the body. The body has a hole that opens in an outer circumferential surface of the body and connects with the transparent terminal.

An endoscopic hood according to a fourth aspect is the endoscopic hood according to the first aspect or the second aspect in which the transparent electrode pattern is provided on a surface of the transparent film, and the conductive film is embedded integrally in the body with the transparent film exposed on an outer circumferential surface of the body and the transparent electrode pattern facing inside the body. The transparent terminal extends to another surface of the transparent film through a through-hole in the transparent film and is exposed on the outer circumferential surface of the body.

An endoscopic hood according to a fifth aspect is the endoscopic hood according to the first aspect or the second aspect in which the transparent electrode pattern is provided on a surface of the transparent film, and the conductive film is embedded integrally in the body with the transparent film exposed on an inner circumferential surface of the body and the transparent electrode pattern facing outside the body. The transparent terminal is exposed through an end face of the body.

An endoscopic hood according to a sixth aspect is the endoscopic hood according to the first aspect or the second aspect in which the transparent electrode pattern is provided on a surface of the transparent film, and the conductive film is embedded integrally in the body with the transparent film exposed on an outer circumferential surface of the body and the transparent electrode pattern facing inside the body. The transparent terminal is exposed through an end face of the body.

An endoscopic hood according to a seventh aspect is the endoscopic hood according to the first aspect or the second aspect in which the transparent electrode pattern is provided on a surface of the transparent film, and the conductive film is embedded integrally in the body with the transparent film exposed on an outer circumferential surface of the body and the transparent electrode pattern facing inside the body. The body has a hole that opens in an inner circumferential surface of the body and connects with the transparent terminal.

An endoscopic hood according to an eighth aspect is the endoscopic hood according to the first aspect or the second aspect in which the transparent electrode pattern is provided on a surface of the transparent film, and the conductive film is embedded integrally in the body with the transparent film exposed on an inner circumferential surface of the body and the transparent electrode pattern facing outside the body. The transparent terminal extends to another surface of the transparent film through a through-hole in the transparent film and is exposed on the inner circumferential surface of the body.

An endoscopic hood according to a ninth aspect is the endoscopic hood according to the first aspect or the second aspect further including an attachment integrated with the body at an end of the body and attachable to the distal end of the insertion portion. The attachment contains a material softer than a material of the body.

The attachment with the above structure is formed from the material softer than the material of the body, allowing easy attachment of the endoscopic hood to the distal end of the insertion portion.

An endoscope according to a tenth aspect includes an insertion portion insertable into a body of a subject, the endoscopic hood according to any one of the third to sixth aspects attached to the distal end of the insertion portion, and at least one wire having one end electrically connected to the transparent terminal and another end electrically connected to an external device.

The endoscope with the above structure includes the fully transparent endoscopic hood. Thus, the endoscopic hood is less likely to reflect light traveling from the endoscope and is less likely to obstruct the field of view of the user with the electrode pattern. This improves visibility for the user in, for example, endoscopic examination. Additionally, the transparent terminal is exposed outside the body or through the end face of the body, allowing easy connection between the transparent terminal and the external device.

An endoscope according to an eleventh aspect includes an insertion portion insertable into a body of a subject, a forceps channel inside the insertion portion, the endoscopic hood according to the seventh aspect or the eighth aspect attached to the distal end of the insertion portion, and at least one wire located through the forceps channel and having one end electrically connected to the transparent terminal and another end electrically connected to an external device.

The endoscope with the above structure includes the fully transparent endoscopic hood. Thus, the endoscopic hood is less likely to reflect light traveling from the endoscope and is less likely to obstruct the field of view of the user with the electrode pattern. This improves visibility for the user in, for example, endoscopic examination. This structure also allows electrical connection between the transparent terminal and the external device through the forceps channel that is preformed in an existing endoscope, thus eliminating the use of a special endoscope.

Advantageous Effects

The endoscopic hood and the endoscope to which the endoscopic hood is attached according to one or more aspects of the present invention can improve visibility for the user of the endoscope.

BRIEF DESCRIPTION OF DRAWINGS

FIG. 16A is a schematic side view of a known endoscopic hood, and FIG. 16B is a schematic sectional view of an endoscope with the known endoscopic hood attached to the distal end of its insertion portion.

DETAILED DESCRIPTION

First Embodiment

Figure 1A:
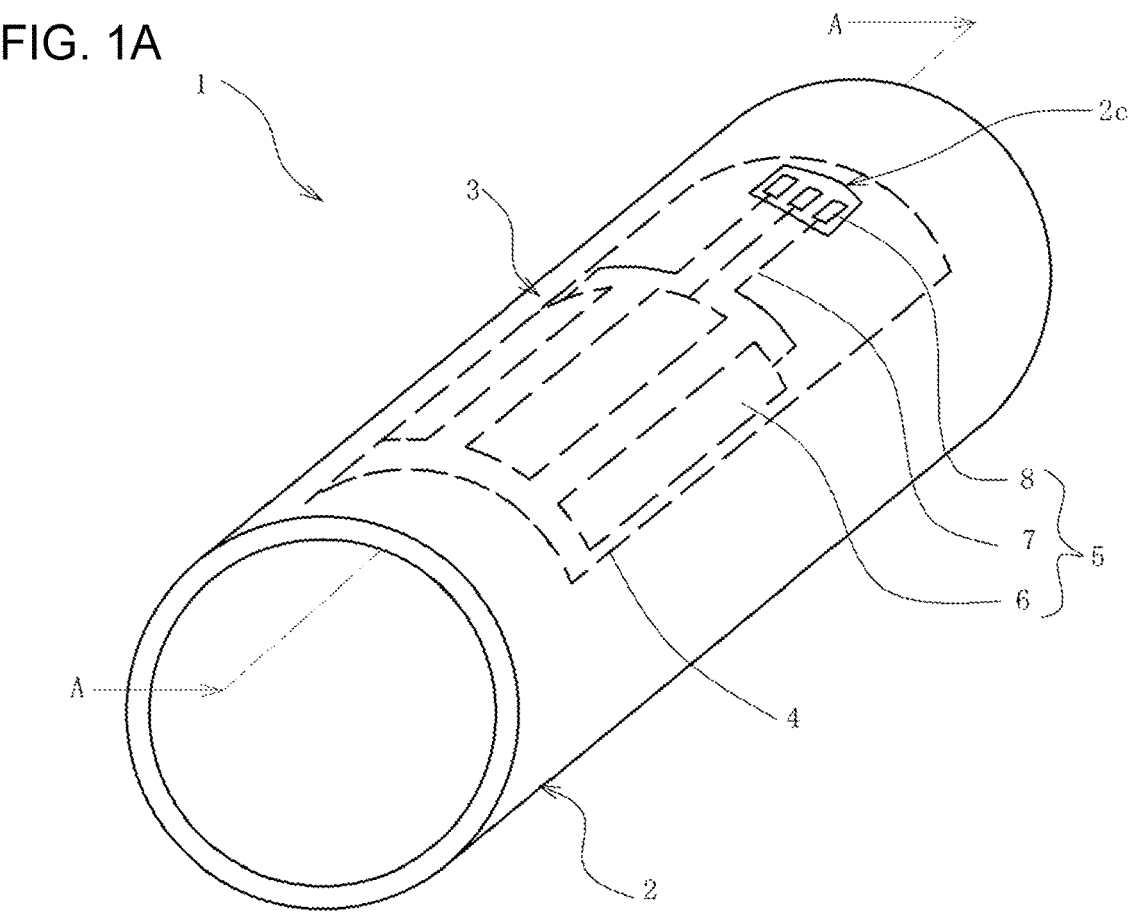
FIG. 1A is a schematic perspective view of an endoscopic hood according to a first embodiment.
Figure 1B:
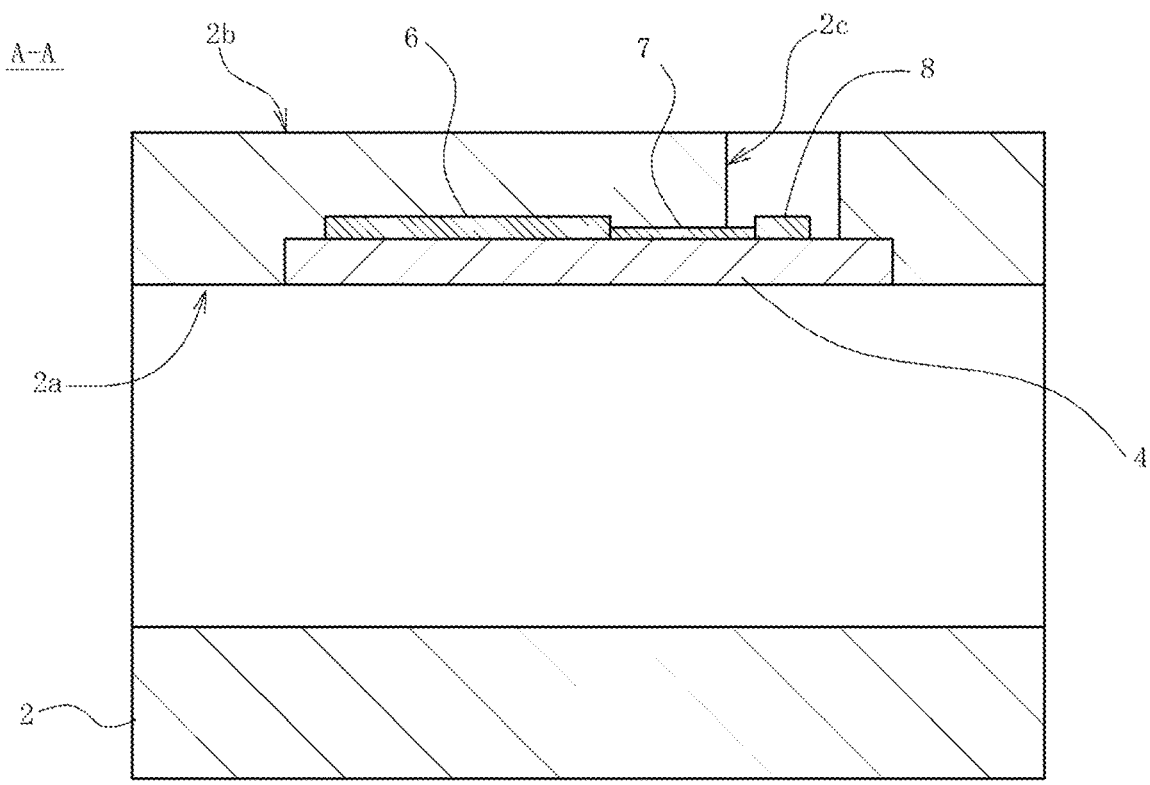
FIG. 1B is a sectional view taken along line A-A in FIG. 1A.

As shown in FIGS. 1A and 1B, an endoscopic hood 1 according to a first embodiment includes at least a cylindrical transparent body 2 having two open ends and a conductive film 3 embedded integrally in the body 2.

Figure 2A:
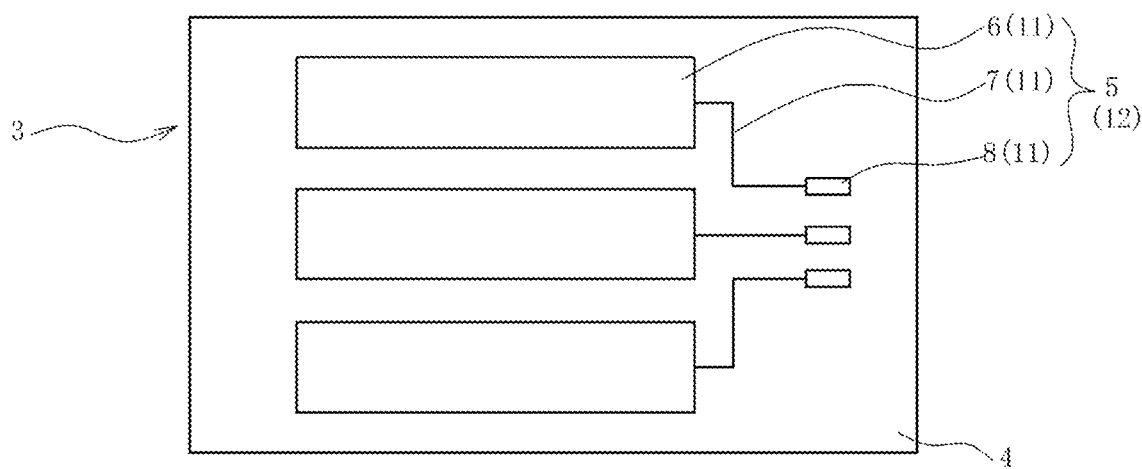
FIG. 2A is a schematic plan view of an example conductive film.

As shown in FIG. 2A, the conductive film 3 includes a transparent electrode pattern 5 provided on a surface of a transparent film 4. The transparent electrode pattern 5 includes three transparent electrodes 6, three transparent wire portions 7 extending from the respective transparent electrodes 6, and three transparent terminals 8 located at ends of the respective transparent wire portions 7. The transparent electrodes 6 and the transparent wire portions 7 may be covered with an insulating layer or an anticorrosive layer.

As shown in FIG. 1B, the conductive film 3 is embedded integrally in the body 2 with the transparent film 4 exposed on an inner circumferential surface 2a of the body 2 and the transparent electrode pattern 5 facing outside the body 2. The transparent film 4 may include a single layer or multiple layers. The conductive film 3 is integrated with the body 2 with no step between the inner circumferential surface 2a of the body 2 and the transparent film 4. The body 2 has a hole 2c that is open in its outer circumferential surface 2b. The single hole 2c is at a position to connect with the three transparent terminals 8.

The conductive film 3 allows the endoscopic hood 1 to have, for example, the functions described below.
  (1) Detecting, for example, the position of the distal end of an insertion portion of an endoscope to which the endoscopic hood is attached, a pressure applied to the insertion portion, or torsion in the insertion portion.
  (2) Preventing fogging of, for example, a lens in the insertion portion.
  (3) Ablating diseased tissue.

The endoscopic hood 1 with the function (1) described above may serve as one of various sensors such as a capacitive touch sensor, a pressure sensor, and a magnetic sensor. The endoscopic hood 1 with the function (2) described above may serve as an anti-fogging heater. The endoscopic hood 1 with the function (3) described above may serve as a tool for radiofrequency ablation.

The material of the body 2 is transparent, insulating plastic such as a polycarbonate resin, a silicone resin, a fluororesin, a thermoplastic elastomer (TPE) resin, or a polyvinyl chloride resin.

The material of the transparent electrode pattern 5 may have a light transmittance (transparency) of 80% or more and a surface resistance (conductivity) of several milliohms to several hundred ohms. The material may be a metal oxide, such as indium oxide, tin oxide, indium tin oxide (ITO), or antimony tin oxide, or a metal, such as gold, silver, copper, platinum, palladium, aluminum, rhodium, or stainless steel. The entire transparent electrode pattern 5 may be formed from the same material. This facilitates formation of the transparent electrode pattern 5.

Figure 2B:
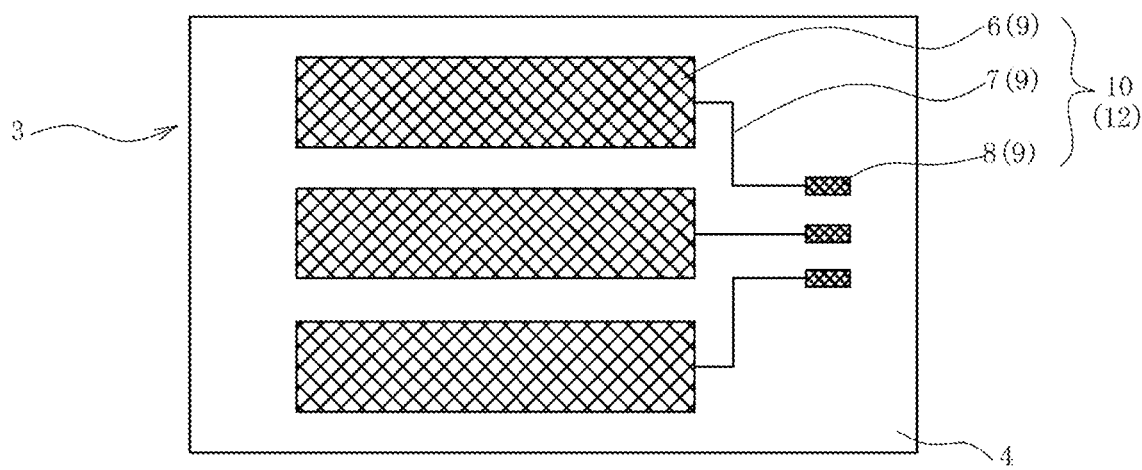
FIG. 2B is a schematic plan view of another example conductive film.

As shown in FIG. 2A, the transparent electrode pattern 5 may be a vapor deposition electrode pattern 12 including a vapor deposition layer 11. As shown in FIG. 2B, the transparent electrode pattern 5 may be a mesh electrode pattern 10 including multiple thin wires 9. The vapor deposition layer 11 included in the vapor deposition electrode pattern 12 may be formed by physical vapor deposition (PVD), such as sputtering, vacuum deposition, or ion plating, or by chemical vapor deposition (CVD) using one of the materials described above. The multiple thin wires 9 included in the mesh electrode pattern 10 may be patterned by etching a thin layer of, for example, one of the materials described above.

Figure 3A:
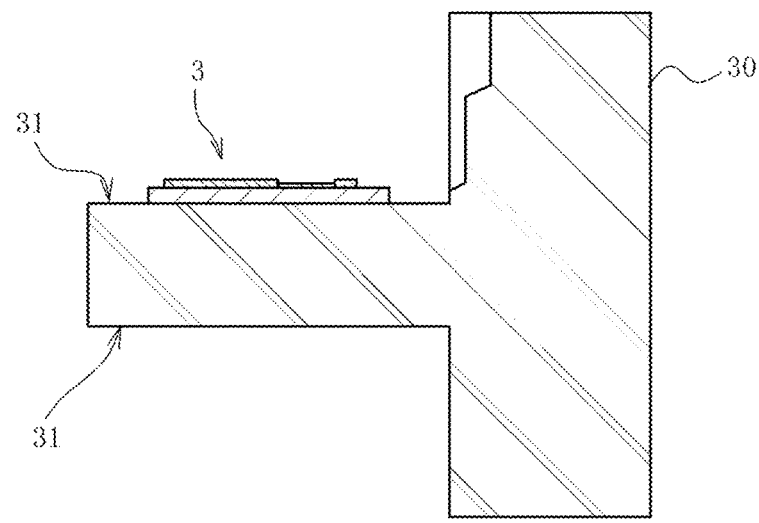
FIGS. 3A to 3C are schematic sectional views of the endoscopic hood in an example manufacturing process.
Figure 3B:
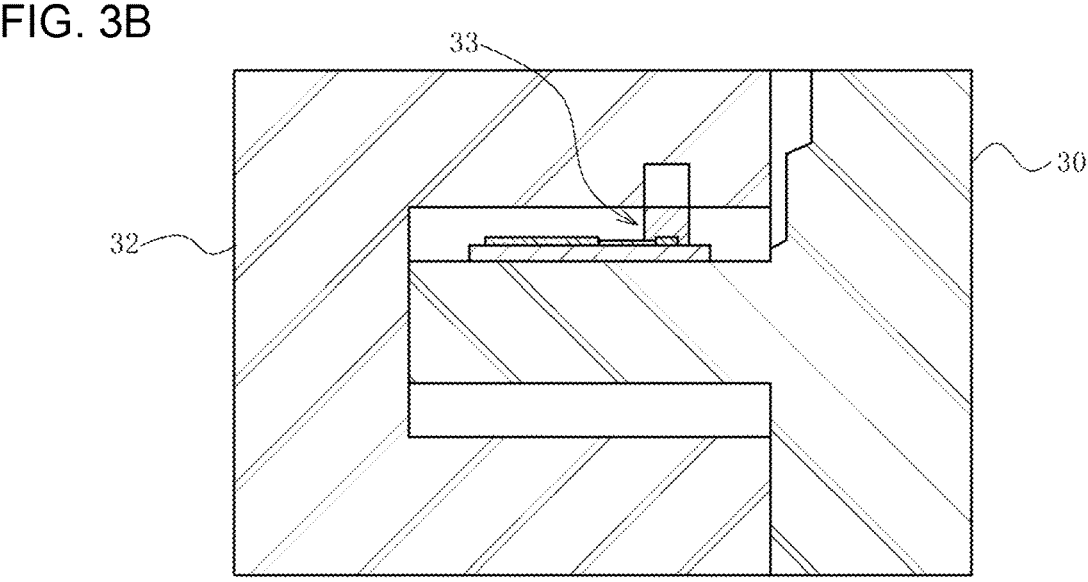
Figure 3C:
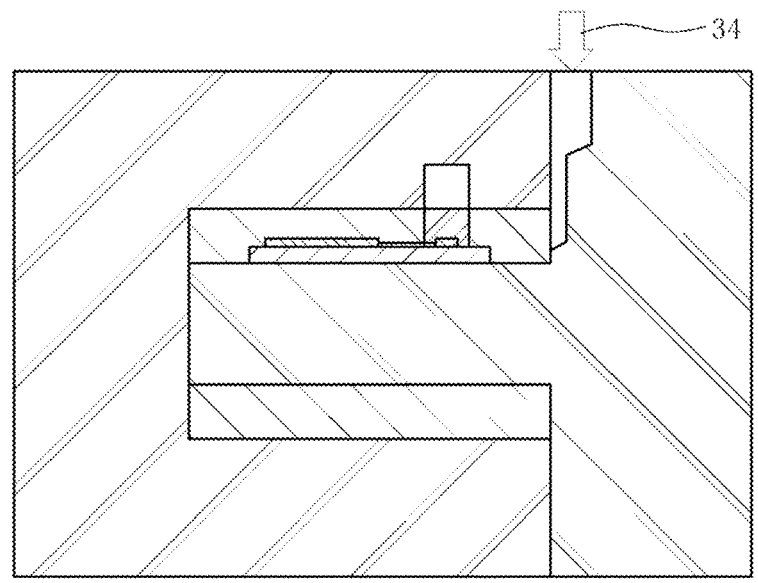

The endoscopic hood 1 including the conductive film 3 may be obtained by insert molding. In the insert molding, the conductive film 3 is first placed on a columnar molding surface 31 of a fixed mold 30 as shown in FIG. 3A. Subsequently, the fixed mold 30 is closed with a movable mold 32 as shown in FIG. 3B. In this state, a pin 33 is placed at a position corresponding to the positions of the transparent terminals 8. The pin 33 can be slid out of the movable mold 32. A molten resin 34 is then injected into the metal mold as shown in FIG. 3C. With the pin 33 placed inside the metal mold, the molten resin 34 is poured in the metal mold excluding the pin 33. This forms the hole 2c connecting with the transparent terminals 8 in the body 2 as a molded product.

In this manner, the resultant endoscopic hood 1 has the conductive film 3 embedded integrally in the body 2. In other words, the resultant endoscopic hood 1 has an integrated structure with no step between the inner circumferential surface 2a of the body 2 and the transparent film 4.

The endoscopic hood 1 according to the first embodiment includes the transparent body 2 and the transparent conductive film 3. Thus, the endoscopic hood 1 is less likely to reflect light traveling from the endoscope and is less likely to obstruct the field of view of the user with the transparent electrode pattern 5. This improves visibility for the user in, for example, an endoscopic examination. The electrode pattern is transparent. Thus, the conductive film 3 integrated with the body 2 can add electrical functions to the endoscopic hood 1 without obstructing the field of view of the user.

Additionally, the conductive film 3 is embedded integrally in the body 2 to reduce the likelihood of entry of, for example, body fluids through an end face of the conductive film 3. Thus, the conductive film 3 is less likely to peel off from the body 2 than a conductive film 3 bonded to the body 2.

The transparent terminals 8 are exposed outside the body 2 through the hole 2c that is open in the outer circumferential surface 2b of the body 2. In other words, the transparent terminals 8 in the transparent electrode pattern 5 are not embedded in the body 2 and are exposed through the hole 2c. This facilitates electrical connection between the transparent terminals 8 and external devices.

Figure 2C:
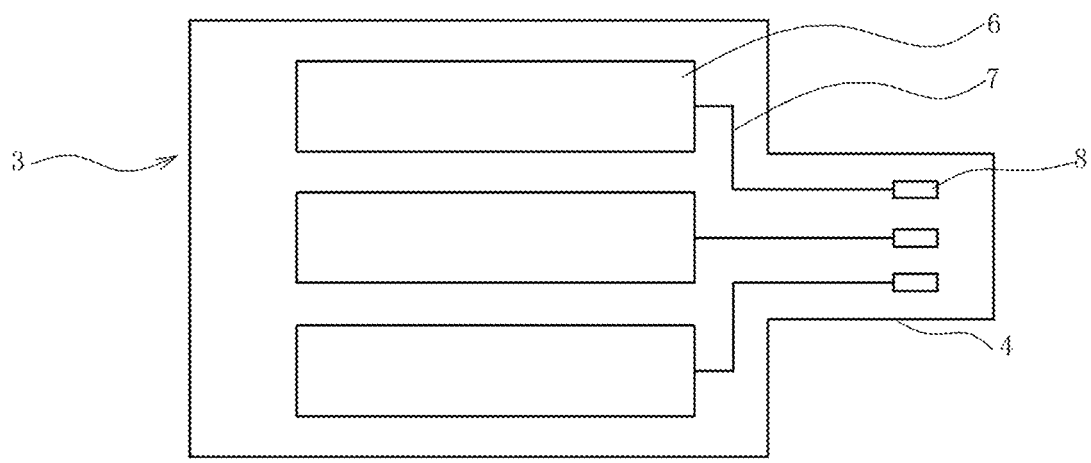
FIG. 2C is a schematic plan view of another example conductive film.

As shown in FIG. 2C, the transparent film 4 may have a shape partially cut away in the areas near a portion in which the transparent terminals 8 are located.

The front surface of the mesh electrode pattern 10 or the vapor deposition electrode pattern 12 may be coated with a blackened layer. This structure can reduce reflection of light traveling from the endoscope, thus improving visibility for the user.

Second Embodiment

An endoscopic hood 1 according to a second embodiment includes the conductive film 3 having a structure different from the structure in the first embodiment. This will be mainly described with reference to FIGS. 4A to 5B. As shown in FIG. 5A, the conductive film 3 includes the transparent electrode pattern 5 on a first surface 4a of the transparent film 4. The transparent electrode pattern 5 includes three transparent electrodes 6, three transparent wire portions 7 extending from the respective transparent electrodes 6, and three transparent terminals 8 located at ends of the respective transparent wire portions 7. As shown in FIG. 5B, the transparent terminals 8 extend to a second surface 4b of the transparent film 4 through through-holes 4c in the transparent film 4.

Figure 4A:
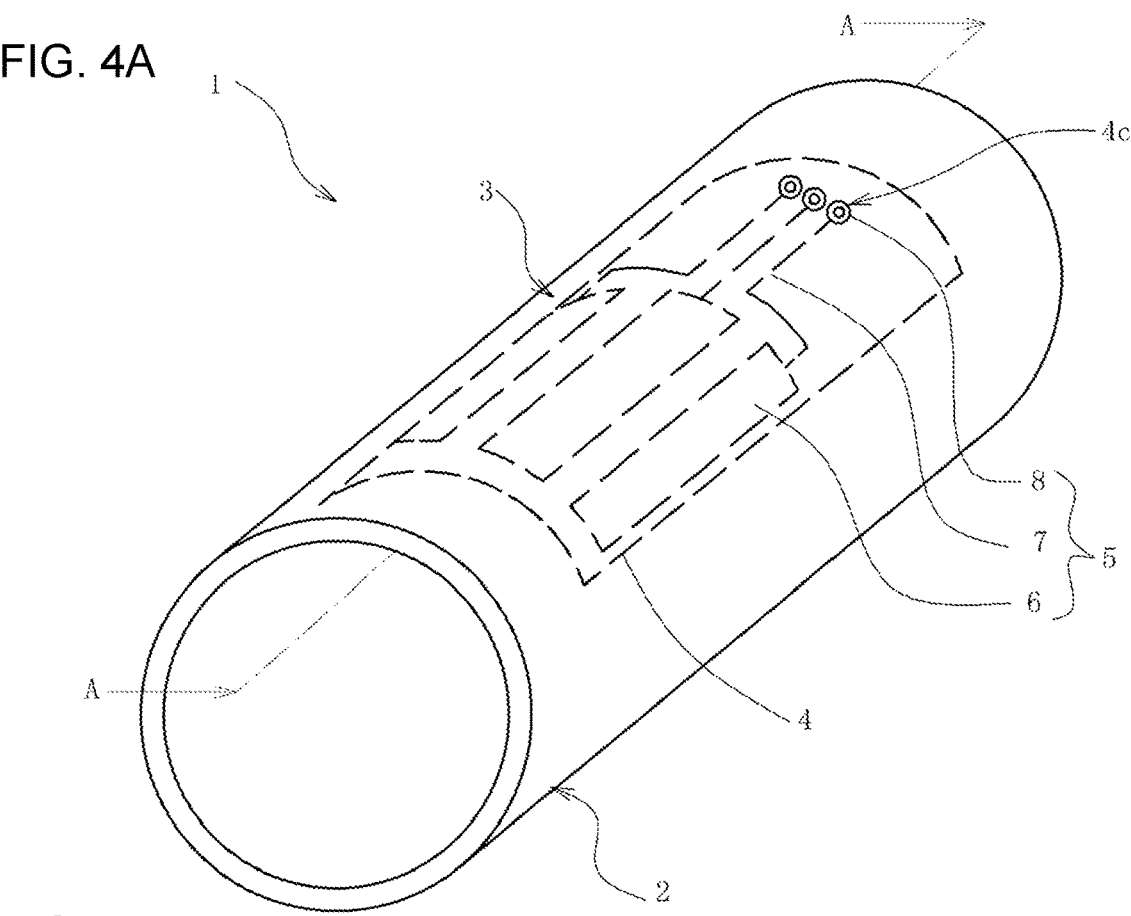
FIG. 4A is a schematic perspective view of an endoscopic hood according to a second embodiment.
Figure 4B:
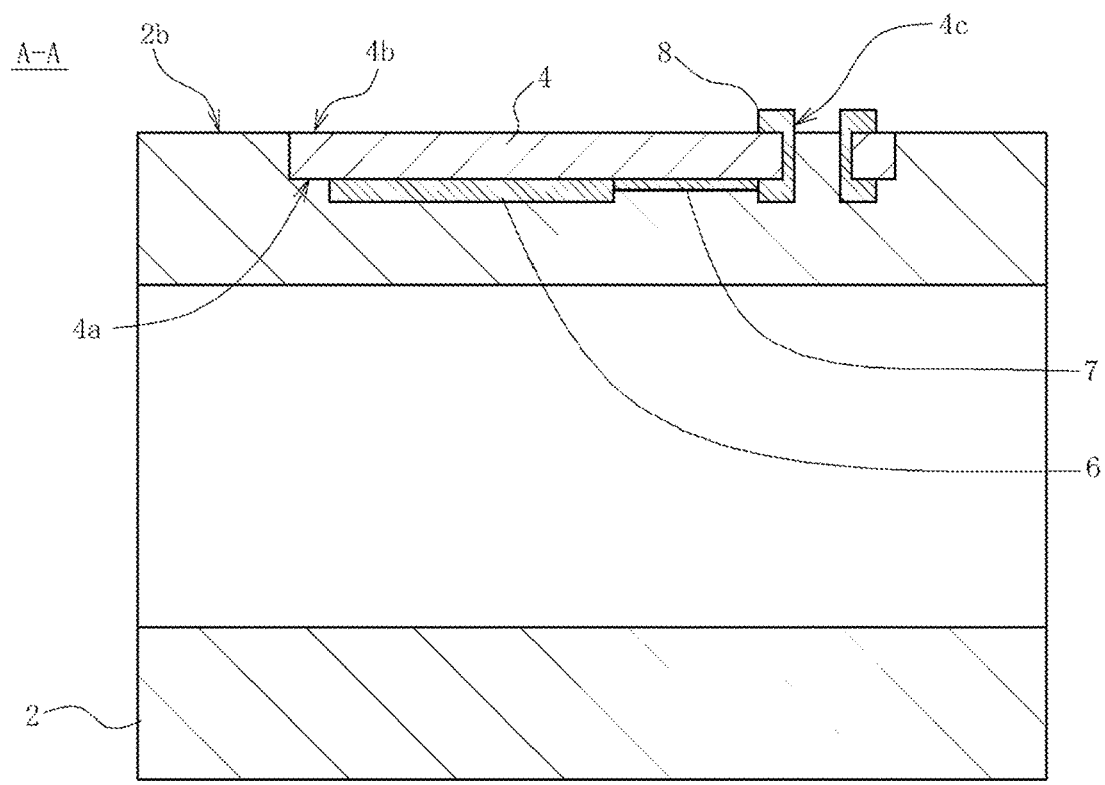
FIG. 4B is a sectional view taken along line A-A in FIG. 4A.
Figure 5A:
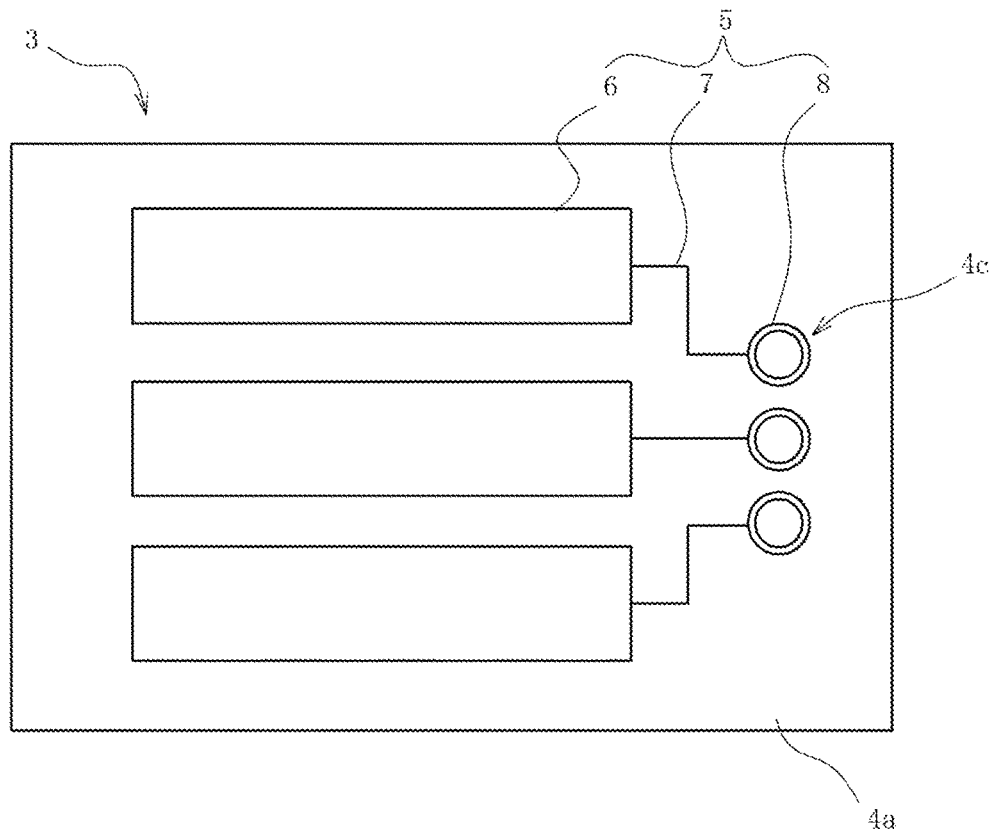
FIG. 5A is a schematic plan view of a conductive film showing a first surface.
Figure 5B:
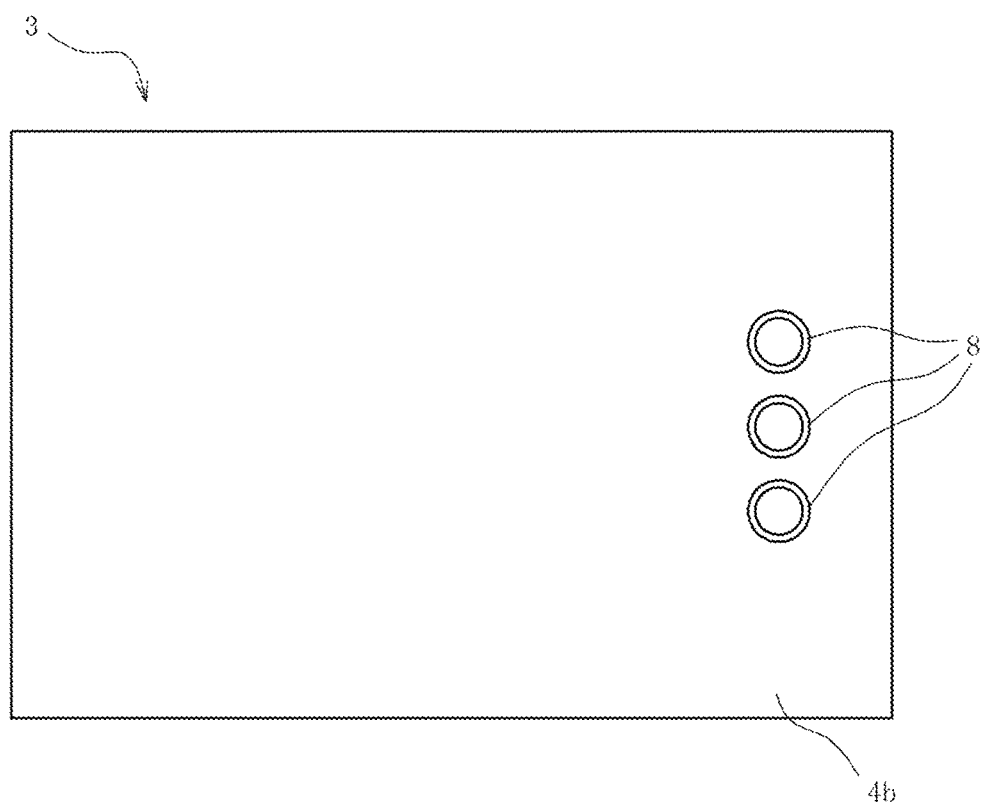
FIG. 5B is a schematic plan view of the conductive film showing a second surface.

As shown in FIG. 4B, each through-hole 4c extends through the transparent film 4. Each transparent terminal 8 extends through the transparent film 4 from the first surface 4a to the second surface 4b along the wall of the corresponding through-hole 4c. The transparent terminals 8 on the first surface 4a of the transparent film 4 are electrically connected to the respective transparent wire portions 7. The through-holes 4c are filled with the body 2. The filled through-holes 4c can reduce the likelihood of expansion of air, deformation, or generation of bubbles in a space inside the through-hole 4c.

As shown in FIG. 4B, the endoscopic hood 1 according to the second embodiment includes the conductive film 3 embedded integrally in the body 2 with the transparent film 4 exposed on an outer circumferential surface 2b of the body 2 and the transparent electrode pattern 5 facing inside the body 2. The transparent terminals 8 extending to the second surface 4b of the transparent film 4 are thus exposed on the outer circumferential surface 2b of the body 2. The conductive film 3 is integrated with the body 2 with no step between the outer circumferential surface 2b of the body 2 and the transparent film 4.

As in the first embodiment, the endoscopic hood 1 according to the second embodiment can be obtained by, for example, insert molding.

In some embodiments, through-holes 4c may receive pins to prevent a molten resin from filling the through-holes 4c. This facilitates insertion of the ends of wires for connection to external devices into the through-holes 4c and fixing with, for example, solder.

The endoscopic hood 1 according to the second embodiment includes the transparent body 2 and the transparent conductive film 3. Thus, the endoscopic hood 1 is less likely to reflect light traveling from the endoscope and is less likely to obstruct the field of view of the user with the transparent electrode pattern 5. This improves visibility for the user in, for example, the endoscopic examination. The electrode pattern is transparent. Thus, the conductive film 3 integrated with the body 2 can add electrical functions to the endoscopic hood 1 without obstructing the field of view of the user.

Additionally, the conductive film 3 is embedded integrally in the body 2 to reduce the likelihood of entry of, for example, body fluids through an end face of the conductive film 3. The conductive film 3 is thus less likely to peel off from the body 2 than a conductive film 3 bonded to the body 2.

The transparent terminals 8 electrically connected to the transparent electrodes 6 and extending to the second surface 4b of the transparent film 4 are exposed on the outer circumferential surface 2b of the body 2. This facilitates electrical connection between the transparent terminals 8 and external devices.

The conductive film 3 is integrated with the body 2 with no step between the outer circumferential surface 2b of the body 2 and the transparent film 4. The endoscopic hood 1 is attached to the insertion portion of an endoscope and can be used to examine the inside of a human body with no such step possibly damaging, for example, cellular tissue or other portions.

Third Embodiment

An endoscopic hood 1 according to a third embodiment includes the transparent terminals 8 exposed at positions different from the positions in the first and second embodiments. This will be mainly described with reference to FIGS. 6A and 6B. As shown in FIG. 6B, the conductive film 3 is embedded integrally in the body 2 with the transparent film 4 exposed on the inner circumferential surface 2a of the body 2 and the transparent electrode pattern 5 facing outside the body 2. The conductive film 3 is integrated with the body 2 with no step between the inner circumferential surface 2a of the body 2 and the transparent film 4. A portion of the transparent film 4, portions of transparent wire portions 7, and transparent terminals 8 are exposed through an end face 2d of the body 2.

The endoscopic hood 1 according to the third embodiment includes the transparent body 2 and the transparent conductive film 3. Thus, the endoscopic hood 1 is less likely to reflect light traveling from the endoscope and is less likely to obstruct the field of view of the user with the electrode pattern 5. This improves visibility for the user in, for example, the endoscopic examination. The electrode pattern is transparent. Thus, the conductive film 3 integrated with the body 2 can add electrical functions to the endoscopic hood 1 without obstructing the field of view of the user.

Additionally, the conductive film 3 is embedded integrally in the body 2 to reduce the likelihood of entry of, for example, body fluids through an end face of the conductive film 3. The conductive film 3 is thus less likely to peel off from the body 2 than a conductive film 3 bonded to the body 2.

The portion of the transparent film 4 and the multiple transparent terminals 8 are exposed through the end face 2d of the body 2, thus allowing simultaneous connection of multiple wires for connection to external devices by crimping.

Figure 6A:
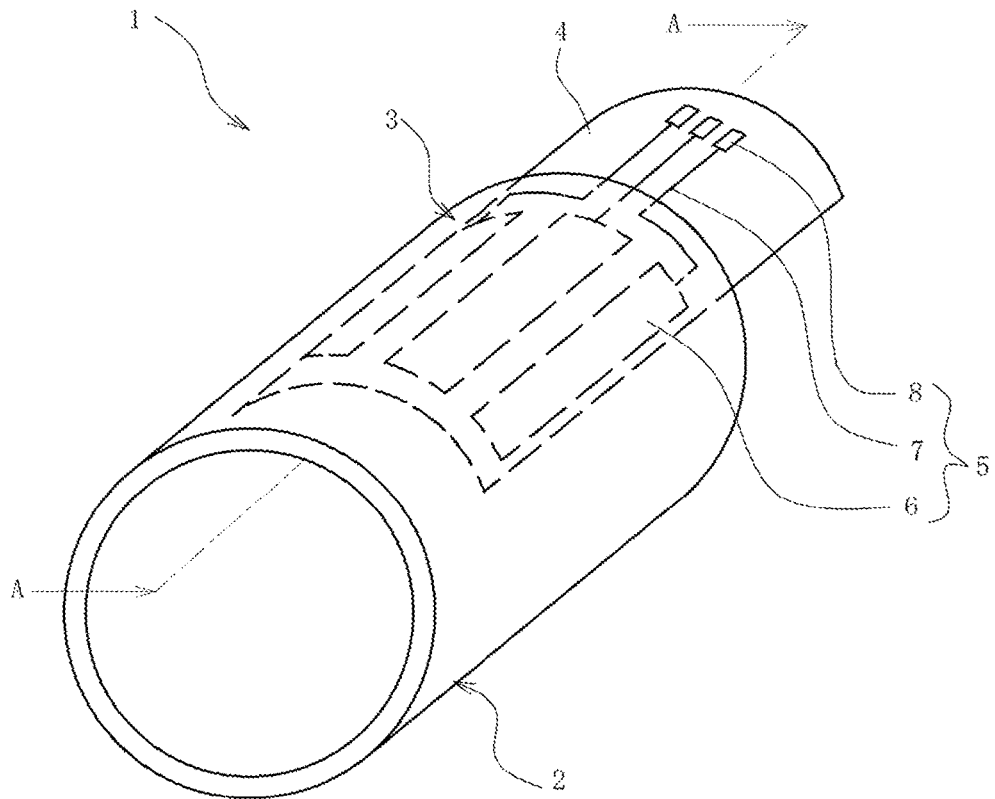
FIG. 6A is a schematic perspective view of an endoscopic hood according to a third embodiment.
Figure 6B:
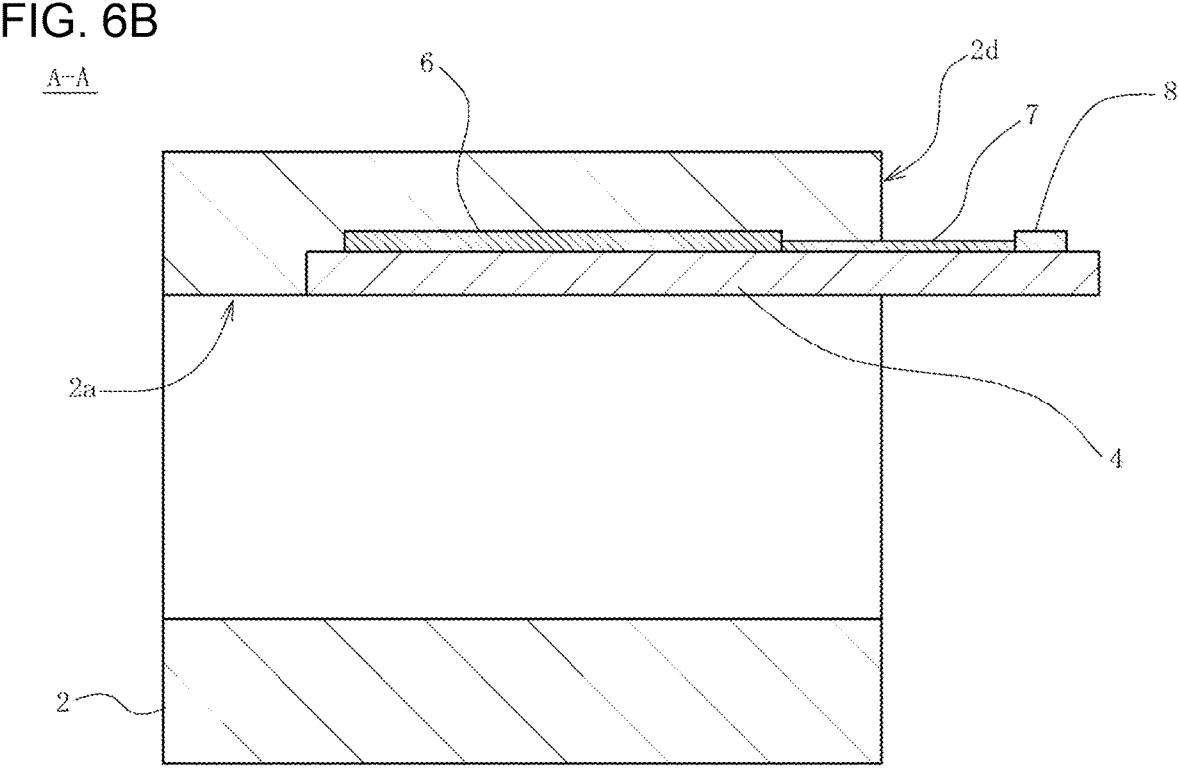
FIG. 6B is a sectional view taken along line A-A in FIG. 6A.

In FIGS. 6A and 6B, the portions of the transparent wire portions 7 are exposed through the end face 2d of the body 2. In some embodiments, the transparent wire portions 7 may not be exposed.

Fourth Embodiment

An endoscopic hood 1 according to a fourth embodiment includes the exposed transparent terminals 8 having orientations different from the orientations in the third embodiment. This will be mainly described with reference to FIGS. 7A and 7B. As shown in FIG. 7B, the conductive film 3 is embedded integrally in the body 2 with the transparent film 4 exposed on the outer circumferential surface 2b of the body 2 and the transparent electrode pattern 5 facing inside the body 2. The conductive film 3 is integrated with the body 2 with no step between the outer circumferential surface 2b of the body 2 and the transparent film 4. A portion of the transparent film 4, portions of transparent wire portions 7, and transparent terminals 8 are exposed through an end face 2d of the body 2.

The endoscopic hood 1 according to the fourth embodiment includes the transparent body 2 and the transparent conductive film 3. Thus, the endoscopic hood 1 is less likely to reflect light traveling from the endoscope and is less likely to obstruct the field of view of the user with the transparent electrode pattern 5. This improves visibility for the user in, for example, the endoscopic examination. The electrode pattern is transparent. Thus, the conductive film 3 integrated with the body 2 can add electrical functions to the endoscopic hood 1 without obstructing the field of view of the user.

Additionally, the conductive film 3 is embedded integrally in the body 2 to reduce the likelihood of entry of, for example, body fluids through an end face of the conductive film 3. The conductive film 3 is thus less likely to peel off from the body 2 than a conductive film 3 bonded to the body 2.

The portion of the transparent film 4 and the multiple transparent terminals 8 are exposed through the end face 2d of the body 2, thus allowing simultaneous connection of multiple wires for connection to external devices by crimping.

The conductive film 3 is integrated with the body 2 with no step between the outer circumferential surface 2b of the body 2 and the transparent film 4. The endoscopic hood 1 is attached to the insertion portion of an endoscope and can be used to examine the inside of a human body with no such step possibly damaging, for example, cellular tissue or other portions.

Figure 7A:
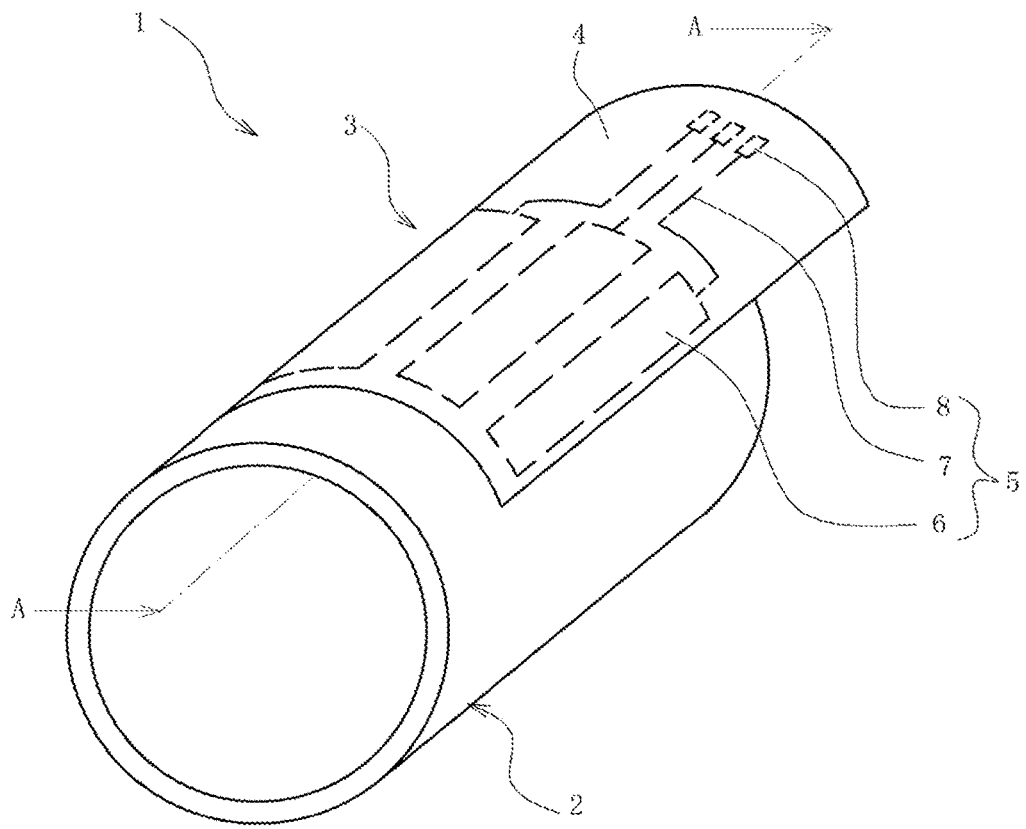
FIG. 7A is a schematic perspective view of an endoscopic hood according to a fourth embodiment.
Figure 7B:
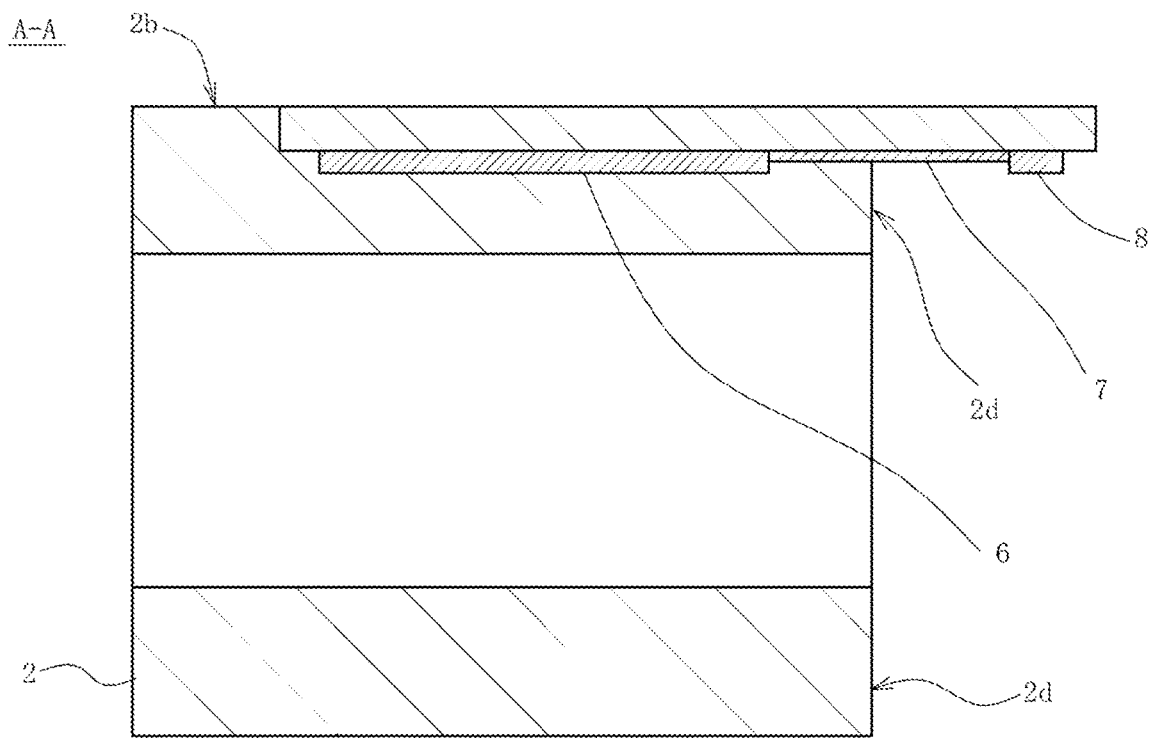
FIG. 7B is a sectional view taken along line A-A in FIG. 7A.

In FIGS. 7A and 7B, portions of the transparent wire portions 7 are exposed through the end face 2d of the body 2. In some embodiments, the transparent wire portions 7 may not be exposed.

Fifth Embodiment

Figure 8A:
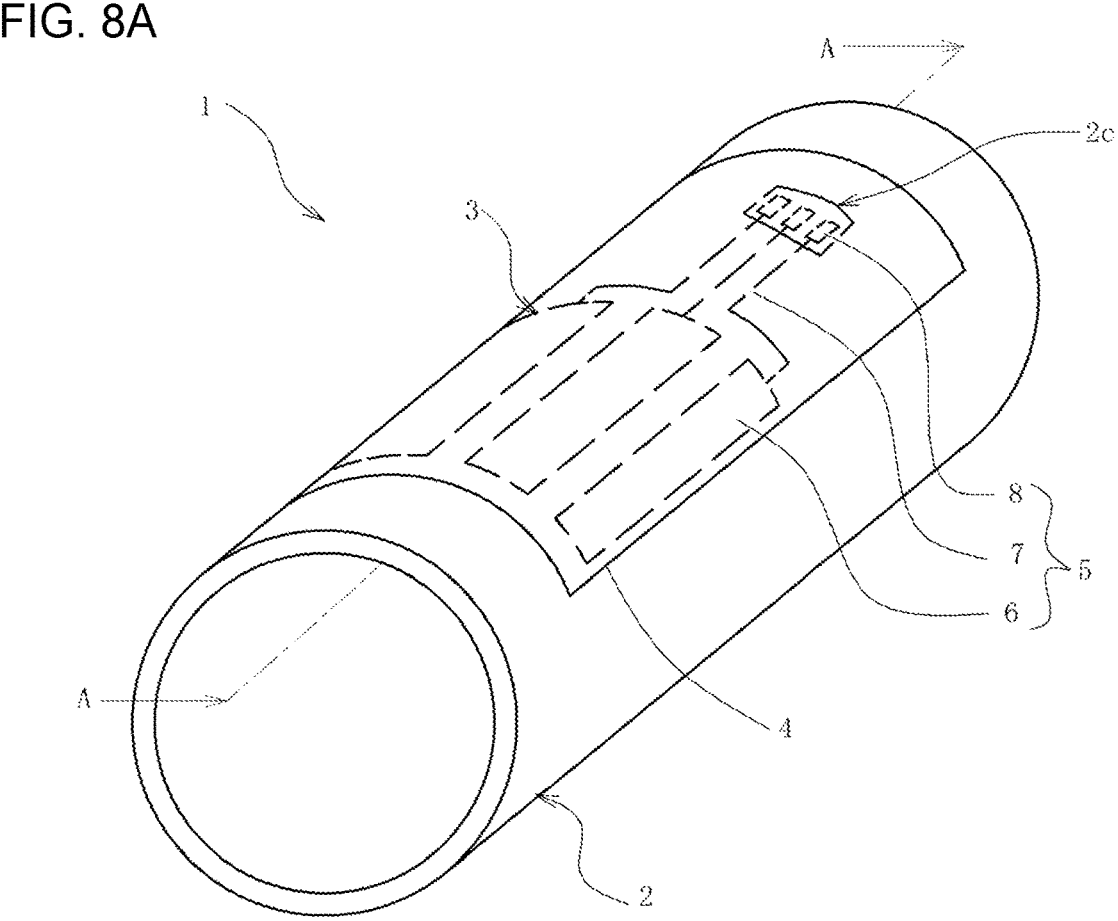
FIG. 8A is a schematic perspective view of an endoscopic hood according to a fifth embodiment.
Figure 8B:
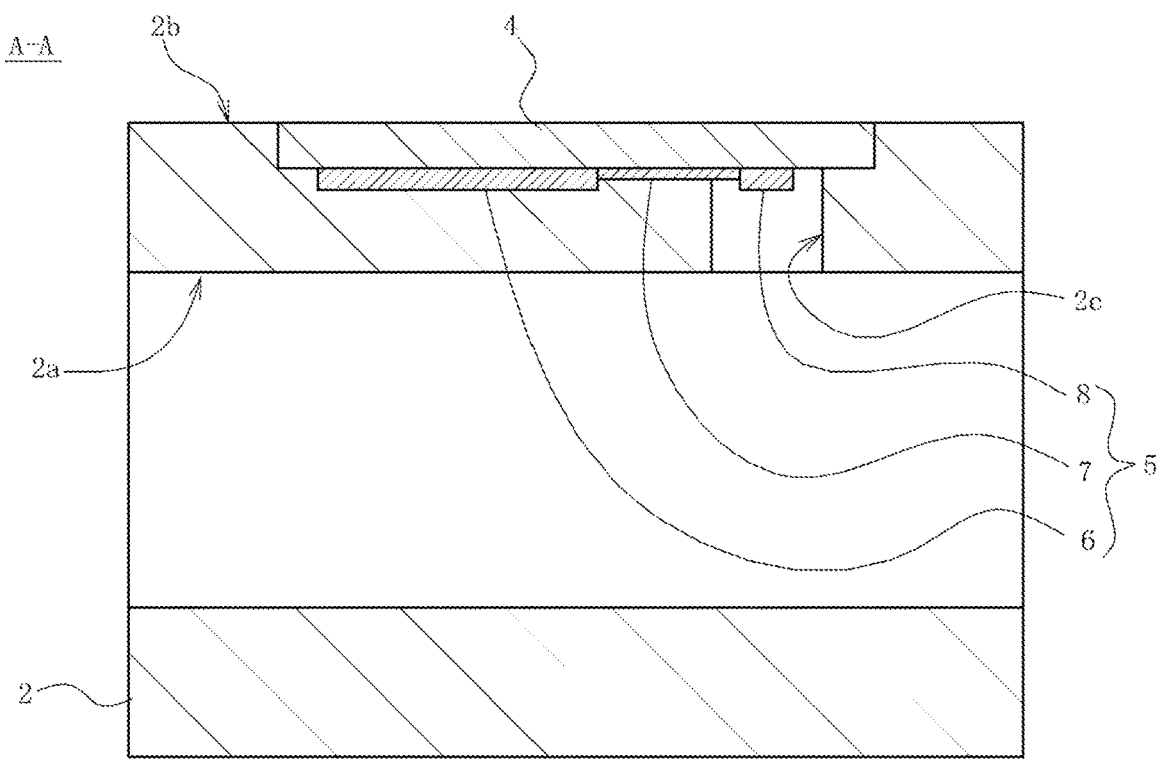
FIG. 8B is a sectional view taken along line A-A in FIG. 8A.

An endoscopic hood 1 according to a fifth embodiment includes transparent terminals 8 exposed in a direction different from the direction in the first embodiment and the hole 2c connecting with the transparent terminals 8 open in a direction different from the direction in the first embodiment. This will be mainly described with reference to FIGS. 8A and 8B. As shown in FIG. 8B, the conductive film 3 is embedded integrally in the body 2 with the transparent film 4 exposed on the outer circumferential surface 2b of the body 2 and the transparent electrode pattern 5 facing inside the body 2. The conductive film 3 is integrated with the body 2 with no step between the outer circumferential surface 2b of the body 2 and the transparent film 4. The body 2 has the hole 2c that is open in its inner circumferential surface 2a. The single hole 2c is at a position to connect with the three transparent terminals 8.

The endoscopic hood 1 according to the fifth embodiment includes the transparent body 2 and the transparent conductive film 3. Thus, the endoscopic hood 1 is less likely to reflect light traveling from the endoscope and is less likely to obstruct the field of view of the user with the transparent electrode pattern 5. This improves visibility for the user in, for example, the endoscopic examination. The electrode pattern is transparent. Thus, the conductive film 3 integrated with the body 2 can add electrical functions to the endoscopic hood 1 without obstructing the field of view of the user.

Additionally, the conductive film 3 is embedded integrally in the body 2 to reduce the likelihood of entry of, for example, body fluids through an end face of the conductive film 3. The conductive film 3 is thus less likely to peel off from the body 2 than a conductive film 3 bonded to the body 2.

The conductive film 3 is integrated with the body 2 with no step between the outer circumferential surface 2b of the body 2 and the transparent film 4. The endoscopic hood 1 is attached to the insertion portion of an endoscope and can be used to examine the inside of a human body with no such step possibly damaging, for example, cellular tissue or other portions.

Sixth Embodiment

Figure 9A:
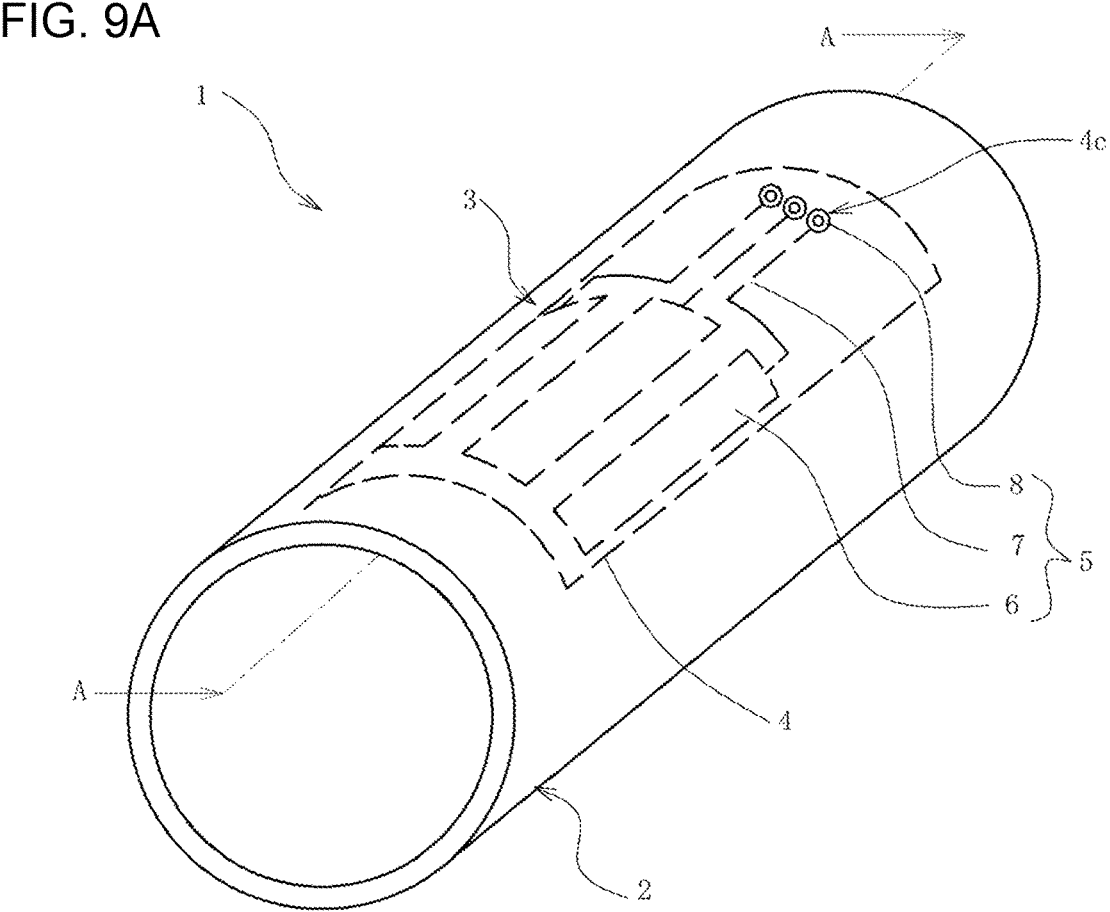
FIG. 9A is a schematic perspective view of an endoscopic hood according to a sixth embodiment.
Figure 9B:
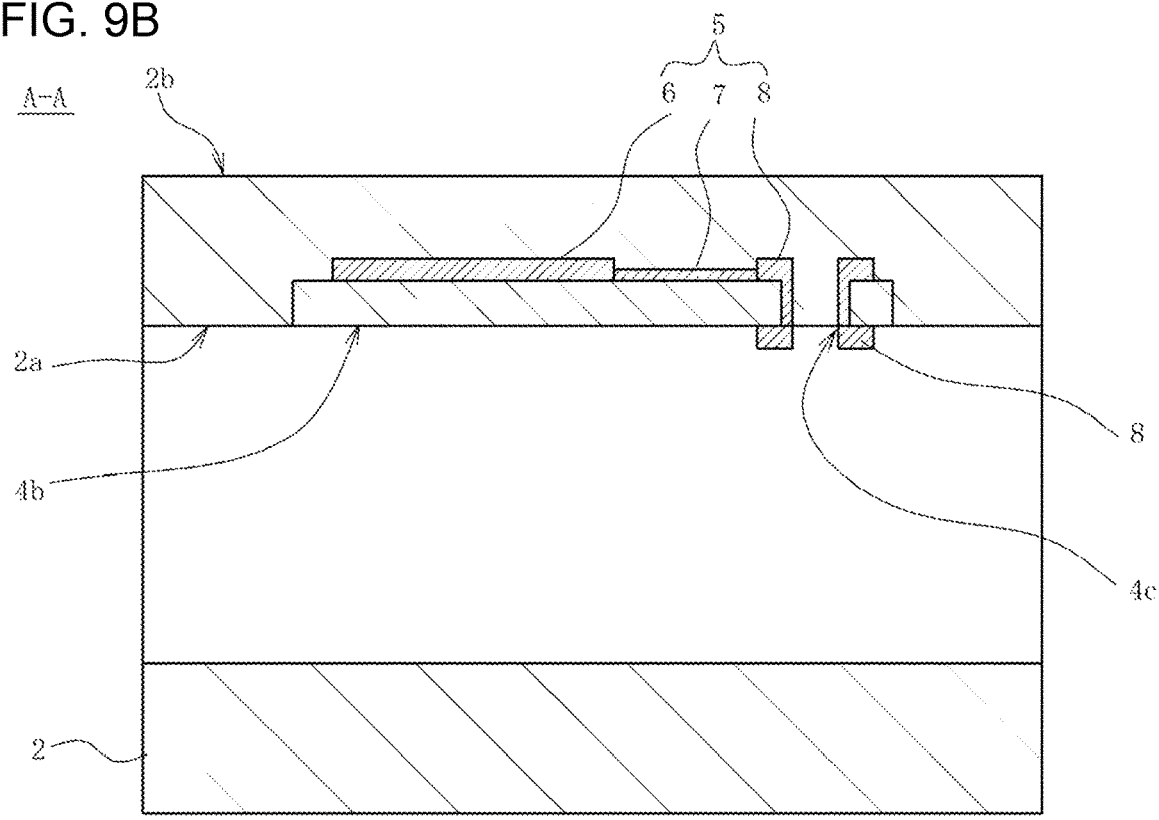
FIG. 9B is a sectional view taken along line A-A in FIG. 9A.

An endoscopic hood 1 according to a sixth embodiment includes the transparent terminals 8 exposed on a surface different from the surface in the second embodiment. This will be mainly described with reference to FIGS. 9A and 9B. As shown in FIG. 9B, the conductive film 3 is embedded integrally in the body 2 with the transparent film 4 exposed on the inner circumferential surface 2a of the body 2 and the transparent electrode pattern 5 facing outside the body 2. The conductive film 3 is integrated with the body 2 with no step between the inner circumferential surface 2a of the body 2 and the transparent film 4.

The endoscopic hood 1 according to the sixth embodiment includes the transparent body 2 and the transparent conductive film 3. Thus, the endoscopic hood 1 is less likely to reflect light traveling from the endoscope and is less likely to obstruct the field of view of the user with the transparent electrode pattern 5. This improves visibility for the user in, for example, the endoscopic examination. The electrode pattern is transparent. Thus, the conductive film 3 integrated with the body 2 can add electrical functions to the endoscopic hood 1 without obstructing the field of view of the user.

Additionally, the conductive film 3 is embedded integrally in the body 2 to reduce the likelihood of entry of, for example, body fluids through an end face of the conductive film 3. The conductive film 3 is thus less likely to peel off from the body 2 than a conductive film 3 bonded to the body 2. This structure is less likely to have any step between the body 2 and the conductive film 3 than when a conductive film 3 is bonded afterward and is thus less likely to have such a step causing bubbles.

Seventh Embodiment

Figure 10A:
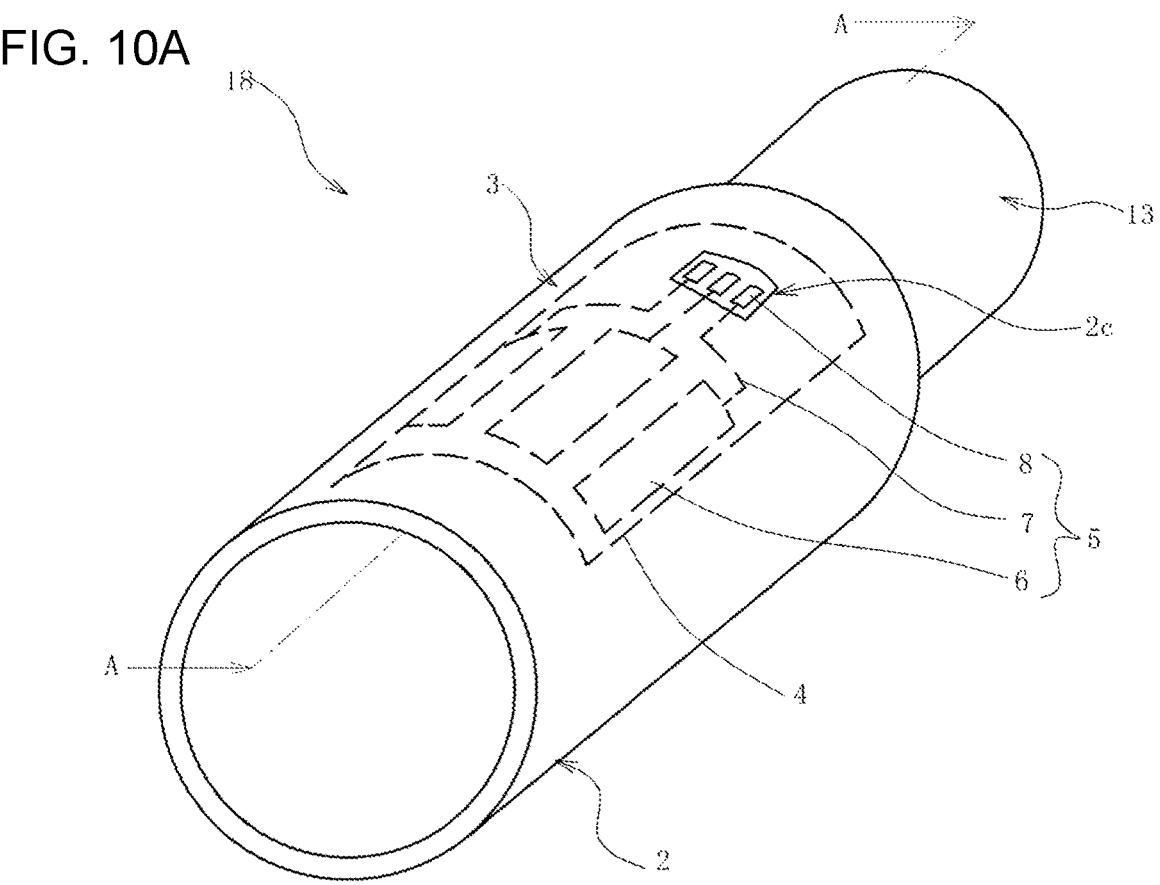
FIG. 10A is a schematic perspective view of an endoscopic hood according to a seventh embodiment.
Figure 10B:
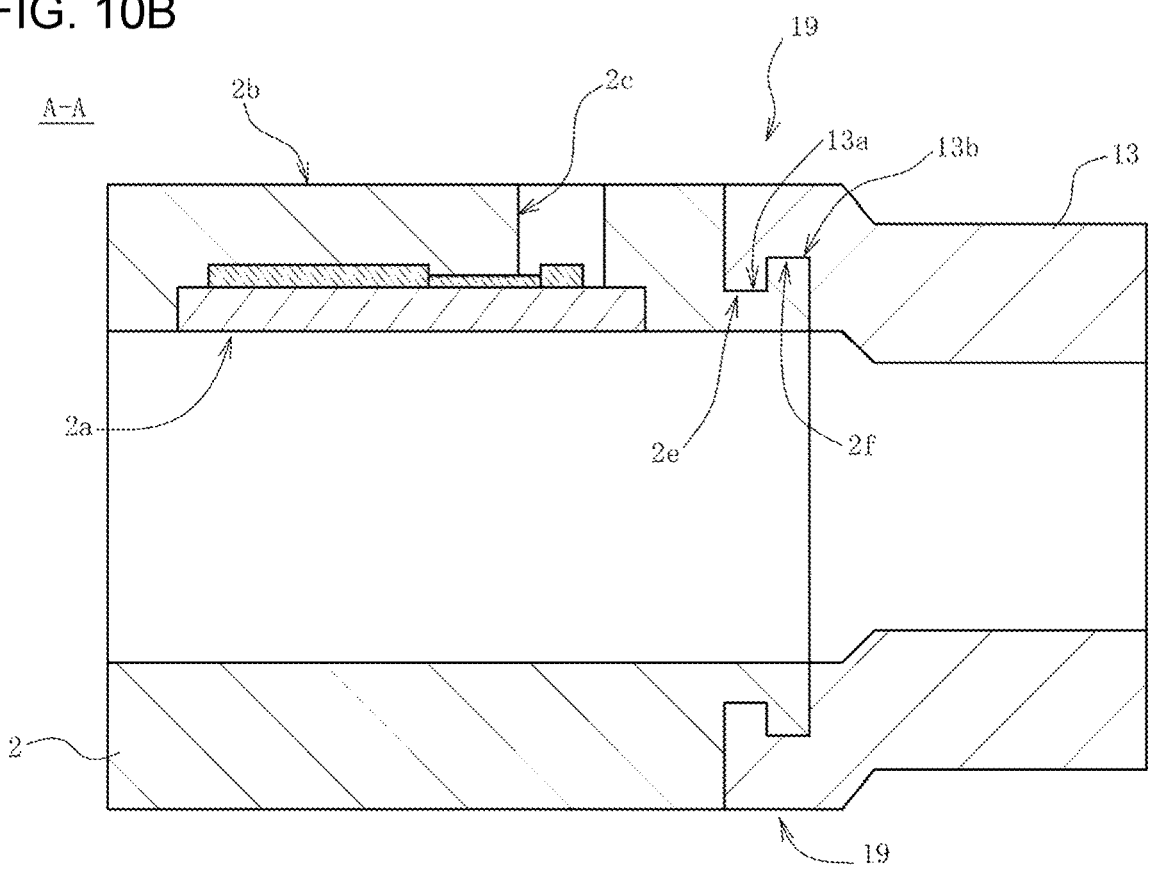
FIG. 10B is a sectional view taken along line A-A in FIG. 10A.

An endoscopic hood 1 according to a seventh embodiment includes an attachment 13 integrated with a body 2 at an end of the body 2, unlike in the first to sixth embodiments. This will now be described with reference to FIGS. 10A and 10B. As shown in FIG. 10B, the endoscopic hood 1 may include a fitting portion 19 between the body 2 and the attachment 13. The fitting portion 19 may have a shape to allow engagement between an end of the body 2 and an end of the attachment 13. In other words, a groove 2e at the end of the body 2 engages with a protrusion 13a at the end of the attachment 13, and a groove 13b at the end of the attachment 13 engages with a protrusion 2f at the end of the body 2 as shown in FIG. 10B.

The attachment 13 is formed from a material softer than the material of the body 2. When, for example, the body 2 is formed from a polycarbonate resin, the attachment 13 may be formed from a silicone resin or a thermoplastic elastomer resin.

In the seventh embodiment, the body 2 is obtained by insert molding, and the attachment 13 is additionally molded by two-color molding. The resultant endoscopic hood 1 includes the body 2 and the attachment 13 that are integrated with each other.

The endoscopic hood 1 according to the seventh embodiment including the attachment 13 formed from a material softer than the material of the body 2 can be easily attached to the distal end of the insertion portion of an endoscope. The fitting portion 19 strengthens the joint between the body 2 and the attachment 13 that are integrated with each other.

First Modification

Figure 11A:
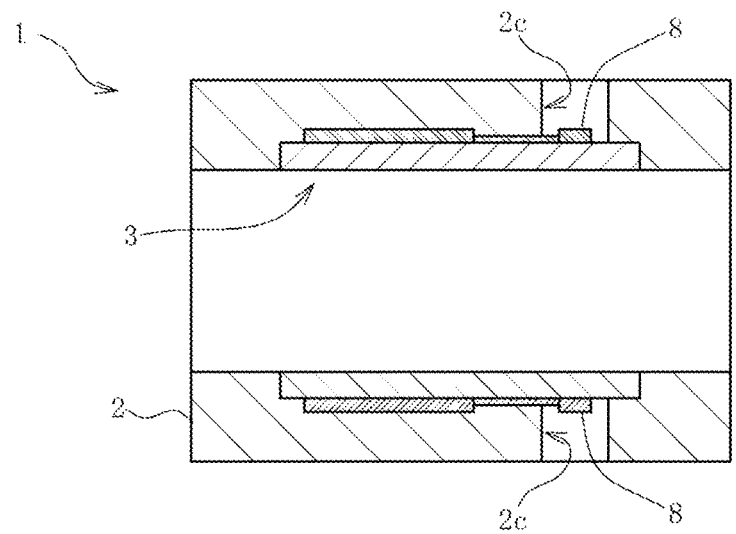
FIG. 11A is a schematic sectional view of an endoscopic hood according to a first modification.

In the first to seventh embodiments, the endoscopic hood 1 includes the single conductive film 3. In some embodiments, the endoscopic hood 1 may include multiple conductive films 3. In this case, the body 2 in each of the first and fifth embodiments includes the hole 2c connecting with the transparent terminals 8 on each conductive film 3. For an endoscopic hood 1 including two conductive films 3, the body 2 has two holes 2c as shown in FIG. 11A.

When, for example, the two conductive films 3 face each other, the conductive films 3 can hold body tissue between them. Thus, the endoscopic hood 1 can serve as a tool for radiofrequency ablation.

Second Modification

Figure 11B:
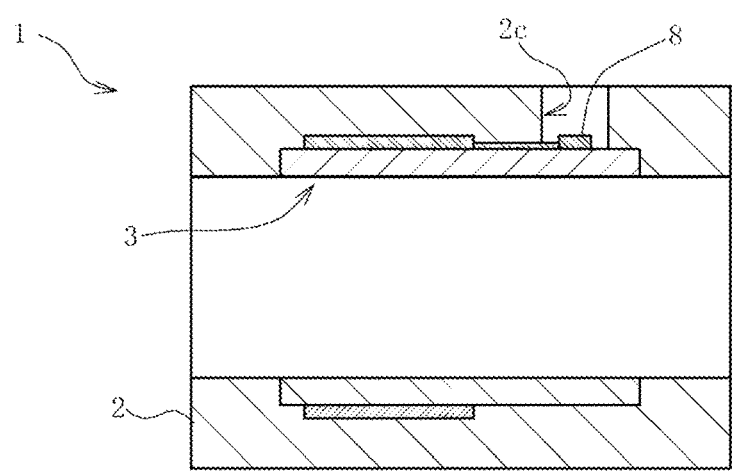
FIG. 11B is a schematic sectional view of an endoscopic hood according to a second modification.

In the first to seventh embodiments, the conductive film 3 extends along less than half the circumference of the body 2. In some embodiments, the conductive film 3 may extend along a distance greater than or equal to half the circumference to less than or equal to the entire circumference as shown in FIG. 11B. Multiple transparent terminals 8 may be at a single position. In this case, the body 2 has a single hole 2c connecting with the transparent terminals 8 in the first and fifth embodiments.

When, for example, a single conductive film 3 is wrapped along the entire circumference of the body 2 and functions as a pressure sensor, the endoscopic hood 1 can detect pressure applied on the entire outer circumferential surface 2b.

Third Modification

Figure 11C:
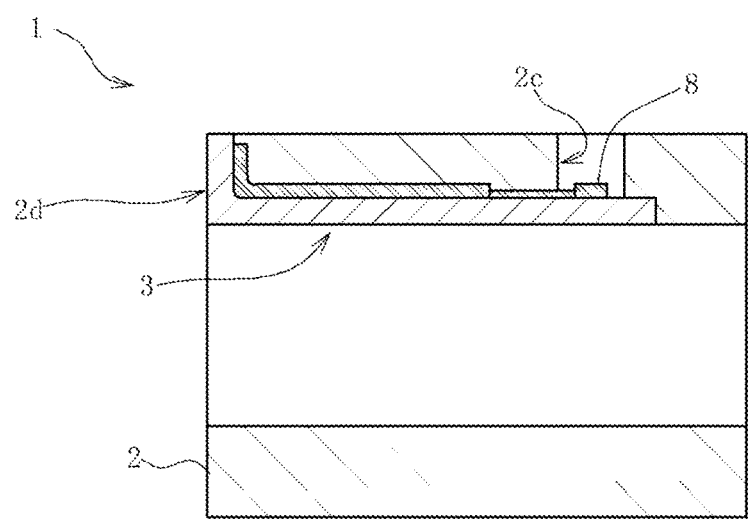
FIG. 11C is a schematic sectional view of an endoscopic hood according to a third modification.

In the first to seventh embodiments, the conductive film 3 is located substantially in the middle of the body 2 as shown in, for example, FIG. 1B. In some embodiments, the conductive film 3 may be integrated with the body 2 with its end extending along the end face 2d of the body 2 as shown in FIG. 11C. The end face 2d may be more frontward than the insertion portion of the endoscope with the endoscopic hood 1. In this structure, the conductive film 3 functions at a position more frontward to achieve higher functional accuracy. For example, the endoscopic hood 1 serving as a magnetic sensor can detect a more frontward position.

Fourth Modification

Figure 12A:
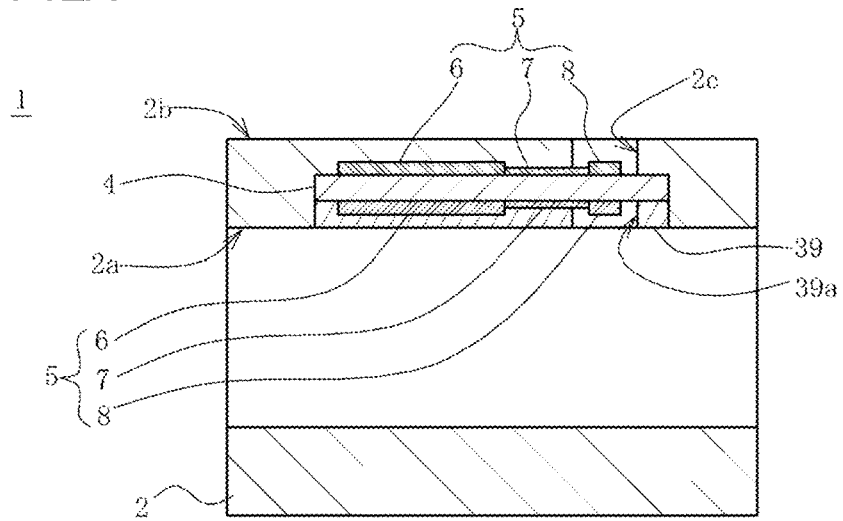
FIGS. 12A to 12C are schematic sectional views of endoscopic hoods according to a fourth modification.
Figure 12B:
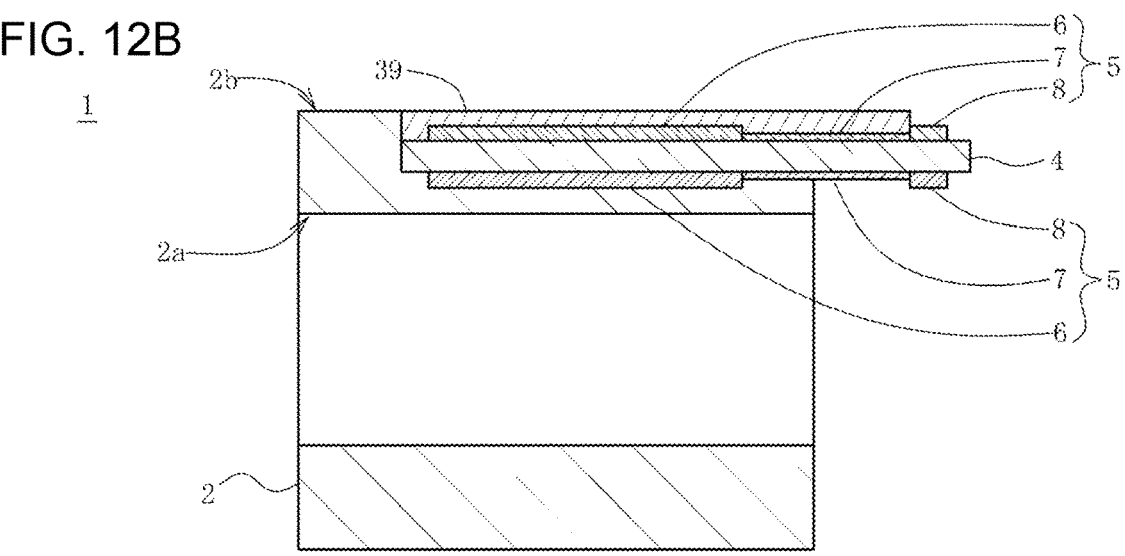
Figure 12C:
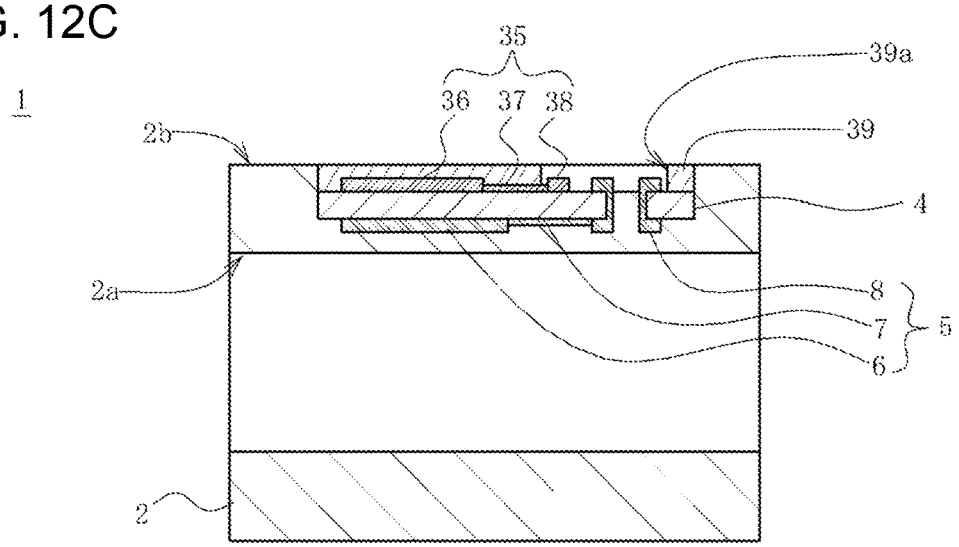

In the first to seventh embodiments, the conductive film 3 includes the electrode pattern 5 on one surface of the transparent film 4. In some embodiments, the conductive film 3 may include the electrode pattern 5 on each surface of the transparent film 4 as shown in FIGS. 12A to 12C. In FIG. 12A, the transparent film 4 includes, on both surfaces, the transparent electrode patterns 5 having the same shape at the same position. The transparent electrode pattern 5 facing inside the body 2 is covered with a cover film 39. The transparent terminals 8 in the covered transparent electrode pattern 5 are exposed on the inner circumferential surface 2a of the body 2 through a hole 39a at a corresponding position of the cover film 39. Transparent terminals 8 in the transparent electrode pattern 5 uncovered with the cover film 39 are exposed on an outer circumferential surface 2b through a hole 2c in the body 2.

In FIG. 12B, the transparent film 4 includes transparent electrode patterns 5 having the same shape at the same position on both surfaces. Transparent electrodes 6 and transparent wire portions 7 both facing outside of a body 2 are covered with a cover film 39. In other words, the transparent terminals 8 on both surfaces are exposed through the end face 2d of the body 2.

In FIG. 12C, the transparent film 4 includes transparent electrode patterns 5 and 35 having different shapes at different positions on both surfaces. The transparent electrode pattern 35 facing outside the body 2 is covered with the cover film 39. The transparent electrode pattern includes transparent electrodes 36, transparent wire portions 37, and transparent terminals 38. The transparent terminals 38 in the covered transparent electrode pattern 35 and transparent terminals 8 extending to the second surface 4b of the transparent film 4 are exposed on the outer circumferential surface 2b of the body 2 through the hole 39a at a corresponding position of the cover film 39.

The cover film 39 may be replaced by, for example, an insulating layer or an anticorrosive layer. In FIGS. 12A and 12B, the transparent electrode patterns on both surfaces may have different shapes at different positions.

Figure 13A:
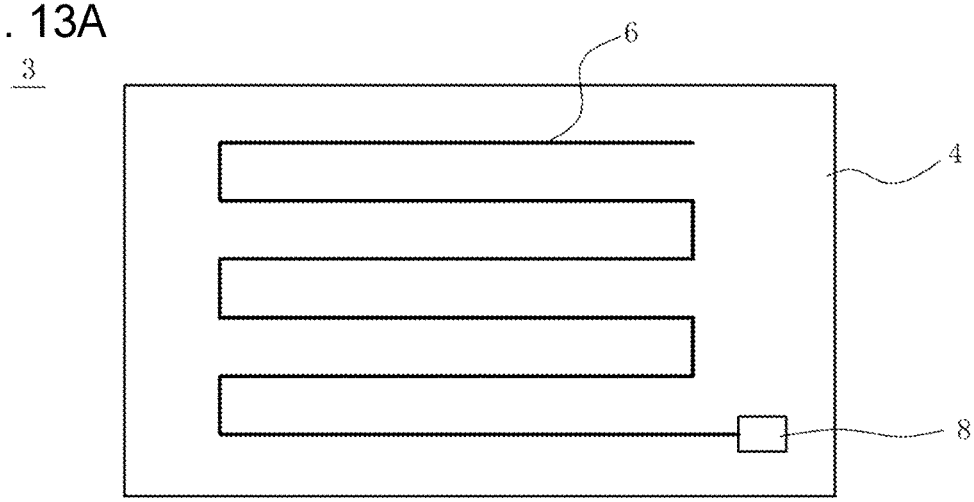
FIGS. 13A to 13C are schematic plan views of other example transparent electrode patterns.
Figure 13B:
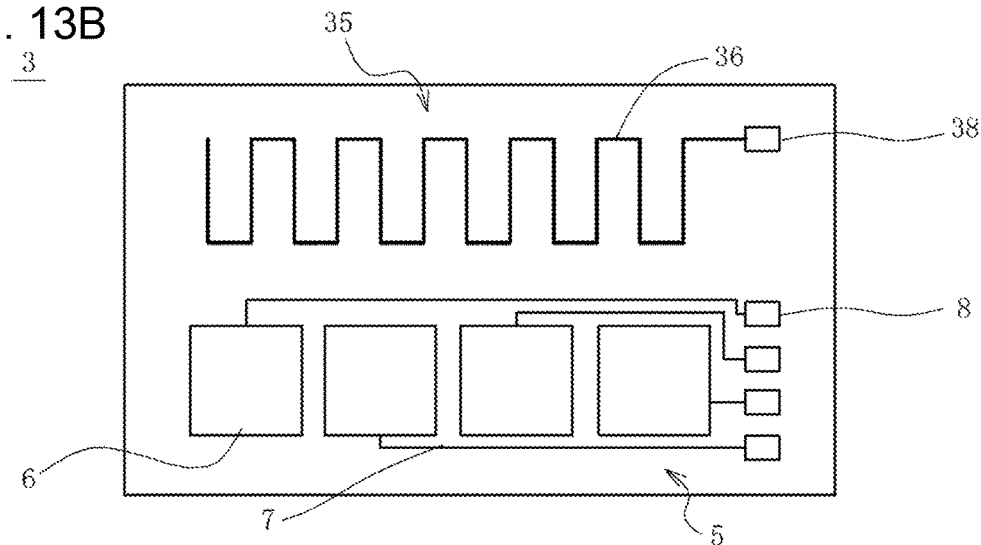
Figure 13C:
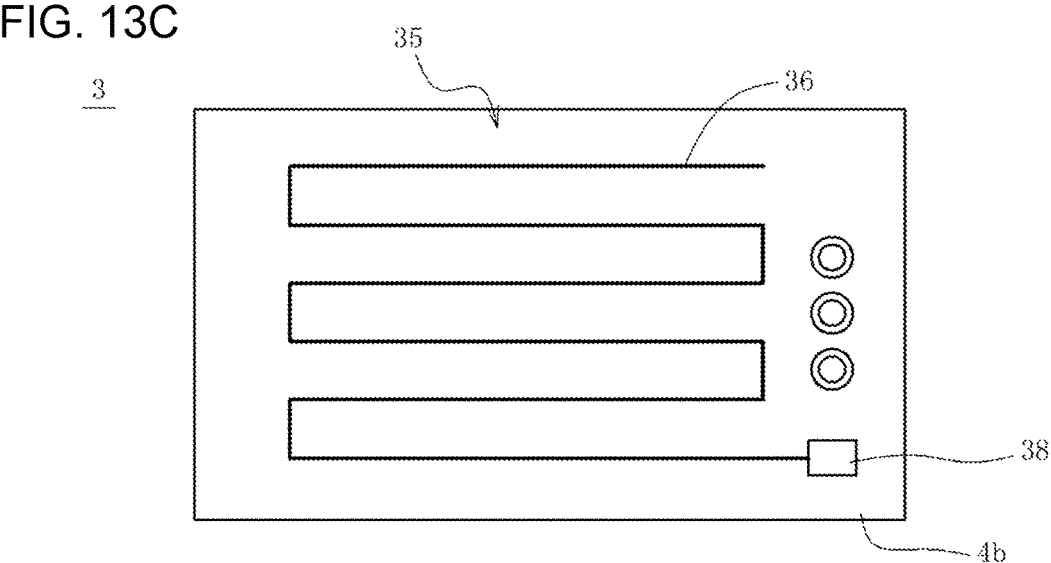

In the first to seventh embodiments and the first to third modifications, the size of the conductive film 3 and the number of the transparent electrode patterns 5 and their shapes and positions may be changed as appropriate for the function or the intended use of the conductive film 3. For example, the transparent electrode 6 may be folded multiple times into a meandered transparent electrode pattern 5 as shown in FIG. 13A. The two types of transparent electrode patterns 5 and 35 having different functions may be located on one surface of a transparent film 4 as shown in FIG. 13B. In FIG. 13B, the transparent electrode pattern 5 functions as a touch sensor, and the transparent electrode pattern 35 functions as an antenna. In other words, the conductive film 3 includes the transparent electrode patterns having different shapes and different functions on one surface of the transparent film 4. In FIG. 13C, the transparent electrode pattern 35 is located on the second surface 4b of the transparent film 4 and functions as, for example, an antenna. An electrode pattern 5 similar to that in FIG. 5A is located on the first surface 4a of the transparent film 4 and functions as, for example, a touch sensor. In other words, the conductive film 3 includes the transparent electrode patterns having different shapes and different functions on both surfaces of the transparent film 4.

Figure 14A:
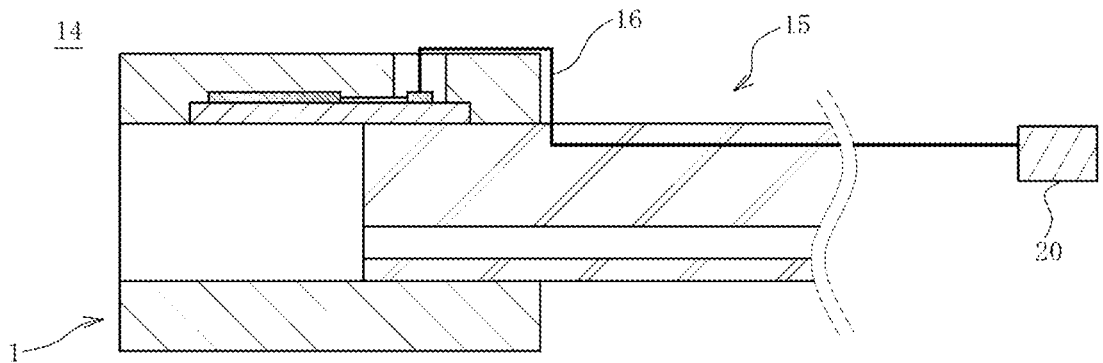
FIG. 14A is a schematic sectional view of an endoscope to which the endoscopic hood according to the first embodiment is attached.

An endoscope 14 shown in FIG. 14A includes an insertion portion 15 insertable into the body of a subject, the endoscopic hood 1 according to the first embodiment attached to the distal end of the insertion portion 15, and at least one wire 16. The wire 16 has one end electrically connected to the transparent terminals 8 and the other end extending through the insertion portion 15 and electrically connected to an external device 20. Such an endoscope 14 including the transparent terminals 8 in the endoscopic hood 1 exposed outside the body 2 allows easy connection of the wire 16.

Figure 14B:
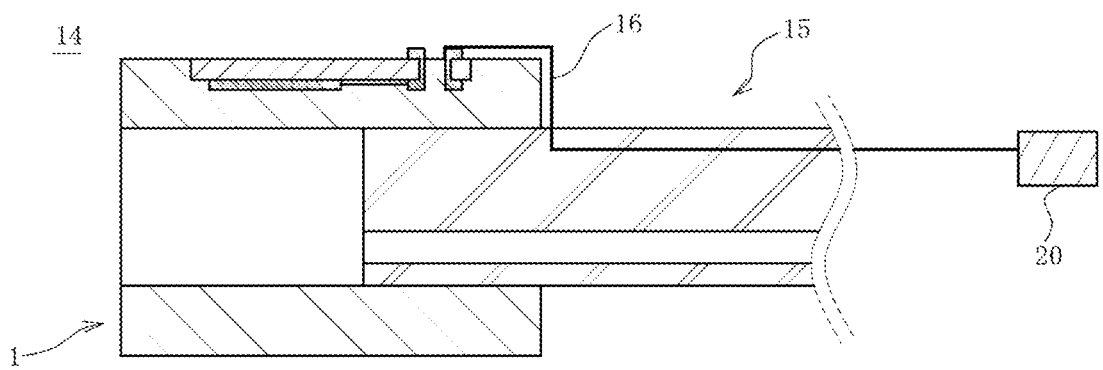
FIG. 14B is a schematic sectional view of an endoscope to which the endoscopic hood according to the second embodiment is attached.
Figure 14C:
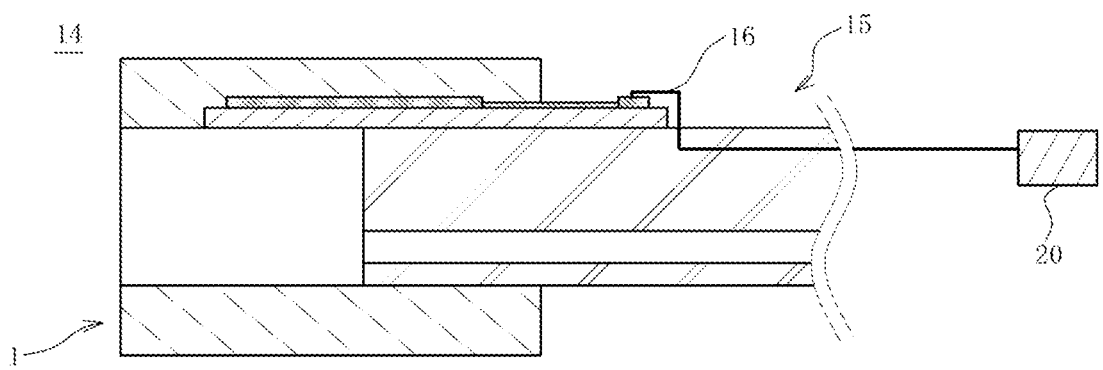
FIG. 14C is a schematic sectional view of an endoscope to which the endoscopic hood according to the third embodiment is attached.
Figure 14D:
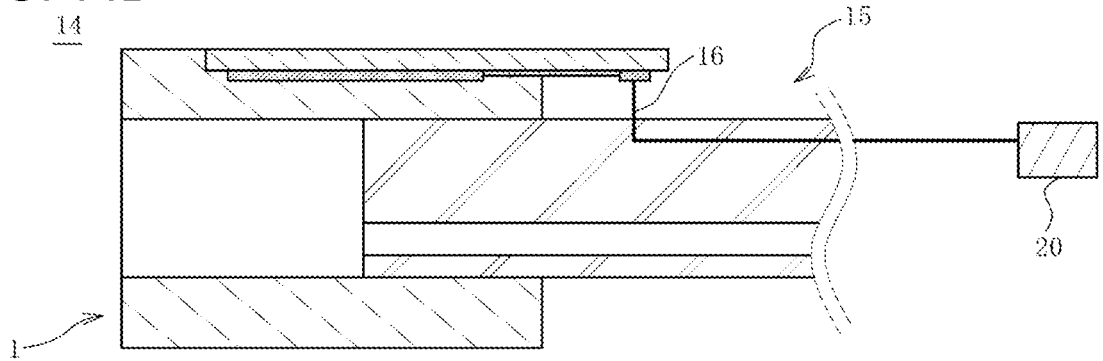
FIG. 14D is a schematic sectional view of an endoscope to which the endoscopic hood according to the fourth embodiment is attached.

The endoscope 14 in FIG. 14B includes the endoscopic hood 1 according to the second embodiment attached to the distal end of an insertion portion 15. The endoscope 14 in FIG. 14C includes the endoscopic hood 1 according to the third embodiment attached to the distal end of an insertion portion 15. The endoscope 14 in FIG. 14D includes the endoscopic hood 1 according to the fourth embodiment attached to the distal end of an insertion portion 15. Similarly to the endoscope 14 in FIG. 14A, these endoscopes 14 each include the transparent terminals 8 included in the endoscopic hood 1 exposed outside the body 2, allowing easy connection of the wire 16.

In FIGS. 14A to 14D, the wire 16 extends through the insertion portion 15. In some embodiments, the wire 16 may be fixed along the outer circumferential surface of the insertion portion 15. In this case, an exposed portion of the wire 16 is covered with an insulating material. In this manner, the wire 16 possibly in contact with the inner surface of, for example, a digestive lumen is less likely to damage the lumen.

In FIGS. 14A and 14B, the wire 16 is located along the outer circumferential surface of the body 2. In some embodiments, the wire 16 may be received in a groove on the outer circumferential surface. Additionally, the wire 16 may be covered with an insulating material. This structure reduces steps between the outer circumferential surface of the body 2 and the wire 16, with the wire 16 being less likely to damage the inner luminal surface of the subject.

Figure 15A:
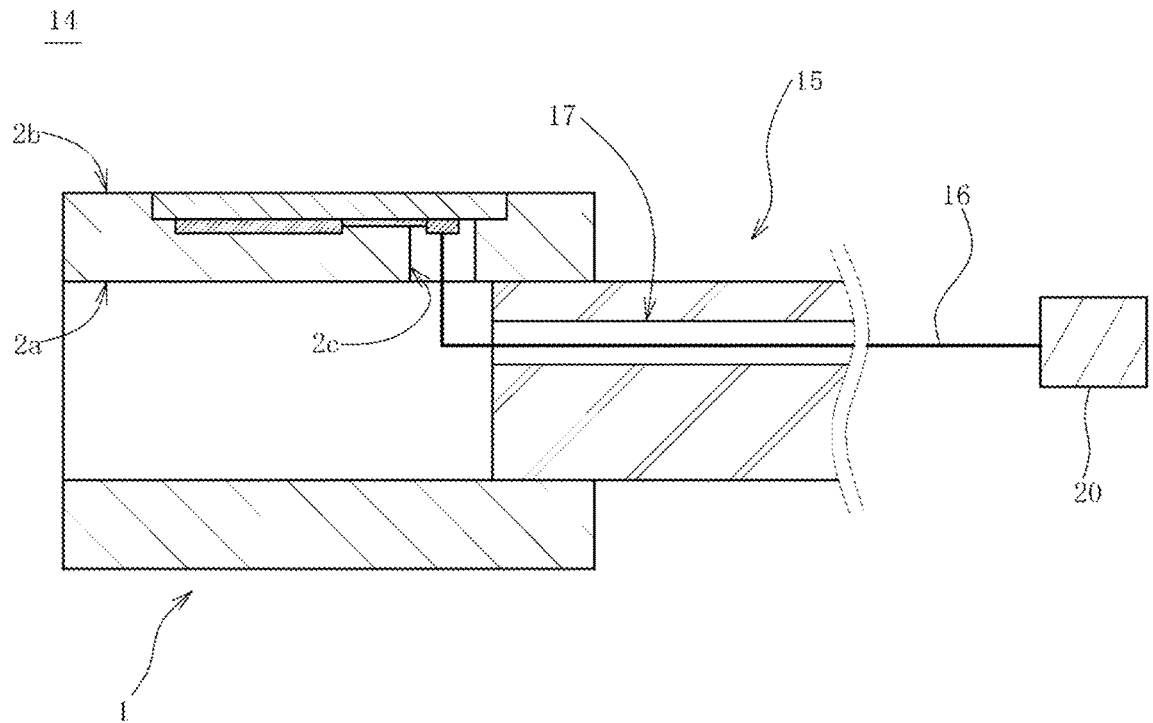
FIG. 15A is a schematic sectional view of an endoscope to which the endoscopic hood according to the fifth embodiment is attached.

The endoscope 14 shown in FIG. 15A includes the insertion portion 15 insertable into the body of a subject, a forceps channel 17 located inside the insertion portion 15, the endoscopic hood 1 according to the fifth embodiment attached to the distal end of the insertion portion 15, and at least one wire 16 extending through the forceps channel 17. The wire 16 has one end electrically connected to the transparent terminals 8 and the other end electrically connected to an external device 20. The wire 16 is covered with an insulating material excluding the electrically connected portions. The wire 16 has a diameter sufficiently smaller than the inner diameter of the forceps channel 17 to allow treatment instruments such as a forceps to extend through the forceps channel 17. A commercially available endoscope including the forceps channel 17, rather than a special endoscope, may be used as such the endoscope 14. The endoscope 14 may thus be easily available.

Figure 15B:
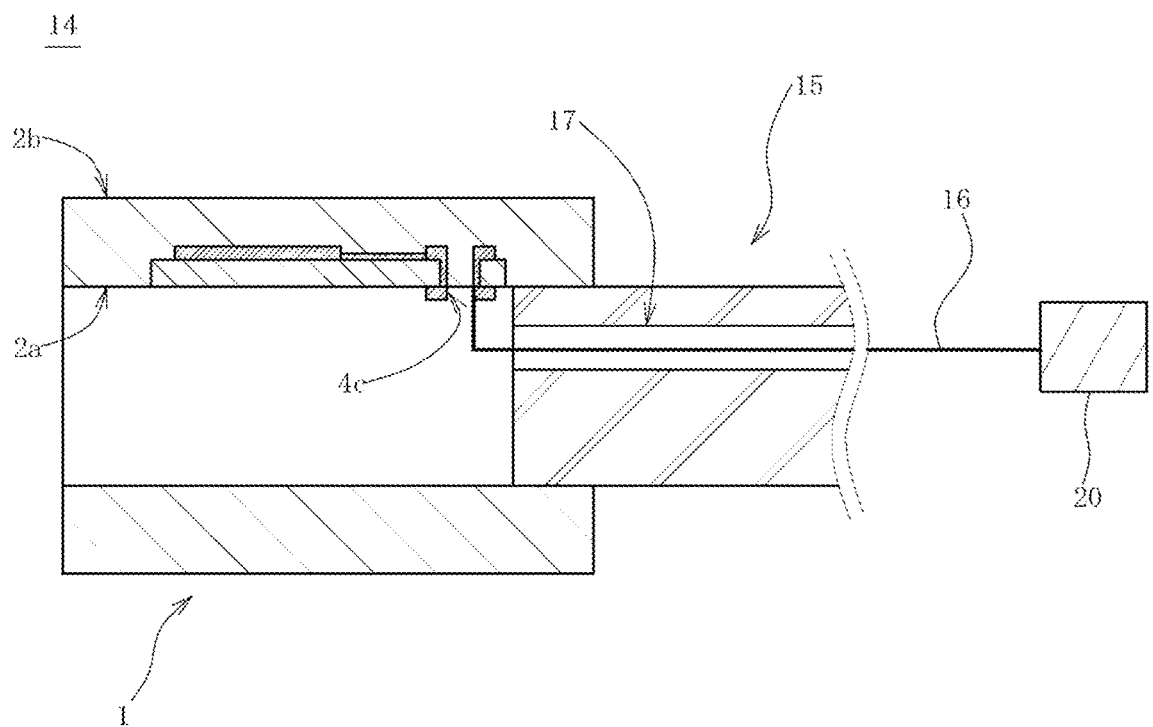
FIG. 15B is a schematic sectional view of an endoscope to which the endoscopic hood according to the sixth embodiment is attached.

An endoscope 14 shown in FIG. 15B has the endoscopic hood 1 according to the sixth embodiment attached to the distal end of an insertion portion 15. Similarly to the endoscope 14 in FIG. 15A, a commercially available endoscope including the forceps channel 17, rather than a special endoscope, may be used as the endoscope 14. The endoscope 14 may thus be easily available.

REFERENCE CHARACTER LIST 1 endoscopic hood
2 body
2a inner circumferential surface
2b outer circumferential surface
2c hole
2d end face
2e groove
2f protrusion
3 conductive film
4 transparent film
4a first surface
4b second surface
4c through-hole
5 transparent electrode pattern
6 transparent electrode
7 transparent wire portion
8 transparent terminal
9 thin wire
10 mesh electrode pattern
11 vapor deposition layer
12 vapor deposition electrode pattern
13 attachment
13a protrusion
13b groove
14 endoscope
15 insertion portion
16 wire
17 forceps channel
18 endoscopic hood
19 fitting portion
20 external device
30 fixed mold
31 molding surface
32 movable mold
33 pin
34 molten resin
35 transparent electrode pattern
36 transparent electrode
37 transparent wire portion
38 transparent terminal
39 cover film
39a hole
100 endoscopic hood
200 body
300 conductive film
400 transparent film
140 endoscope
150 insertion portion

The invention claimed is:

1. An endoscopic hood comprising:
a body formed of a transparent cylinder having two open ends; and
a conductive film insert-molded in the body such that the conductive film is provided integrally embedded in the body, the conductive film including a transparent film and a transparent electrode pattern on the transparent film, the transparent electrode pattern including a transparent electrode, a transparent wire portion extending from the transparent electrode, and a transparent terminal at an end of the transparent wire portion, the transparent terminal being exposed from the body.

2. The endoscopic hood according to claim 1, wherein the transparent electrode pattern is a mesh electrode pattern including a plurality of thin wires or a vapor deposition electrode pattern including a vapor deposition layer.

3. The endoscopic hood according to claim 1, wherein the transparent electrode pattern is provided on a surface of the transparent film, and the conductive film is provided integrally embedded in the body with the transparent film exposed on an inner circumferential surface of the body and the transparent electrode pattern facing outside the body, and
the body has a hole that opens in an outer circumferential surface of the body and connects with the transparent terminal.

4. An endoscope, comprising:
an insertion portion insertable into a body of a subject;
the endoscopic hood according to claim 3, the endoscopic hood being attached to a distal end of the insertion portion; and
at least one wire having one end electrically connected to the transparent terminal and another end electrically connected to an external device.

5. The endoscopic hood according to claim 1, wherein the transparent electrode pattern is provided on a surface of the transparent film, and the conductive film is provided integrally embedded in the body with the transparent film exposed on an outer circumferential surface of the body and the transparent electrode pattern facing inside the body, and
the transparent terminal extends to another surface of the transparent film through a through-hole in the transparent film and is exposed on the outer circumferential surface of the body.

6. The endoscopic hood according to claim 1, wherein the transparent electrode pattern is provided on a surface of the transparent film, the transparent film is exposed on an inner circumferential surface or an outer circumferential surface of the body, the transparent electrode pattern faces outside or inside the body, and the transparent electrode is provided integrally embedded in the body, and a portion of the transparent film and the transparent terminal on the portion of the transparent film protrude outside from the body.

7. The endoscopic hood according to claim 1, wherein the transparent electrode pattern is provided on a surface of the transparent film, and the conductive film is provided integrally embedded in the body with the transparent film exposed on an outer circumferential surface of the body and the transparent electrode pattern facing inside the body, and the body has a hole that opens in an inner circumferential surface of the body and connects with the transparent terminal.

8. An endoscope, comprising:

an insertion portion insertable into a body of a subject;

a forceps channel inside the insertion portion;

the endoscopic hood according to claim 7, the endoscopic hood being attached to a distal end of the insertion portion; and at least one wire located through the forceps channel and having one end electrically connected to the transparent terminal and another end configured to be electrically connected to an external device.

9. The endoscopic hood according to claim 1, wherein the transparent electrode pattern is provided on a surface of the transparent film, and the conductive film is provided integrally embedded in the body with the transparent film exposed on an inner circumferential surface of the body and the transparent electrode pattern facing outside the body, and the transparent terminal extends to another surface of the transparent film through a through-hole in the transparent film and is exposed on the inner circumferential surface of the body.

10. The endoscopic hood according to claim 1, further comprising:

an attachment integrated with the body at an end of the body and attachable to a distal end of an insertion portion of an endoscope, the attachment comprising a material softer than a material of the body.

\* \* \* \* \*